US005707830A

United States Patent [19]
Calos

[11] Patent Number: 5,707,830
[45] Date of Patent: Jan. 13, 1998

[54] AUTONOMOUS REPLICATON SYSTEM FOR MAMMALIAN CELLS

[75] Inventor: Michele Pamela Calos, Woodside, Calif.

[73] Assignee: The Board of Trustees of the Leland Stanford Junior University, Stanford, Calif.

[21] Appl. No.: 826,534

[22] Filed: Apr. 2, 1997

Related U.S. Application Data

[63] Continuation of Ser. No. 246,867, May 20, 1994, abandoned.

[51] Int. Cl.$^6$ .............................. C12P 21/00; C12N 15/85
[52] U.S. Cl. .................. 435/69.1; 435/172.3; 435/320.1; 435/352; 435/366
[58] Field of Search .............................. 435/69.1, 172.1, 435/172.3, 320.1, 325, 352, 353, 354, 358, 366, 369, 370

[56] References Cited

U.S. PATENT DOCUMENTS

| | | | |
|---|---|---|---|
| 4,686,186 | 8/1987 | Sugden | 435/243 |
| 5,144,019 | 9/1992 | Rossi et al. | 536/23.1 |
| 5,190,931 | 3/1993 | Inouye | 435/91.32 |

OTHER PUBLICATIONS

Ridgway, "Vectors A Survey of Molecular Cloning Vectors and Their Uses", Eds. Rodriguez and Denhardt, 1988, Butterworth Publishers, Stoneham, MA, pp. 467–492.
Adams, A., "Replication of Latent Epstein–Barr Virus Genomes in Raji Cells," J. Virol. 61:5:1743–1746 (1987).
Anderson, W.F., "Human Gene Therapy," Science 256:808–813 (1992).
Ashman, C.R., et al., "High Spontaneous Mutation Frequency of BPV Shuttle Vector, " Somatic Cell and Molecular Genetics 11:499–504 (1985).
Belt, P.B.G.M. et al., "Construction and Properties of an Epstein–Barr–virus–derived cDNA expression vector for human cells," Gene 84:407–417 (1989).
Burke, D. T. et al., "Cloning of Large Segments of Exogenous DNA into Yeast by Means of Artificial Chromosome Vectors," Science 236:806–812 (1987).
Caddle, M.S. et al., "Analysis of the autonomous replication behavior in human cells of the dihydrofolate reductase putative chromosomal origin of replication," Nucl. Acids Res. 20:22:5971–59778 (1982).
Coutelle, C., et al., Archives of Disease in Childhood, The Journal of the British Paediatric Association, Annotations, "Gene therapy for cystic fibrosis," vol. 68(4), Apr. 1993.
Drinkwater, N.R., et al., "Chemically induced mutagenesis in a shuttle vector with a low–background mutant frequency," Proc. Natl. Acad. Sci. 83:3402–3406 (1986).
DuBridge, R.B. et al., "Recombinant shuttle vectors for the study of mutation in mammalian cells," Mutagenesis 3:1:1–9 (1988).
DuBridge, R.B. et al., "Analysis of Mutation in Human Cells by Using an Epstein–Barr Virus Shuttle System," Mol. and Cel. Biol. 7:1:379–387 (1987).

Gilbert,D.M. et al., "Bovine Papilloma Virus Plasmids Replicate Randomly in Mouse Fibroblasts throughout S Phase of the Cell Cycle," Cell 50:59–68 (1987).
Haase, S.B. et al., "Improved EBV shuttle vectors," Mutation Res. 220:125–132 (1989).
Haase, S.B. et al., "Replication control of autonomously replicating human sequences," Nucl. Acids Res 19:18:5053–5058 (1991).
Haase, S.B. et al., "Transcription Inhibits the Replication of Autonomously Replicating Plasmids in Human Cells," Molec. and Cel. Biol. 14:4:2516–2524 (1994).
Heinzel, S.S. et al., "Use of Simian Virus 40 Replication to Amplify Epstein–Barr Virus Shuttle Vectors in Human Cells," J. Virol. 62:10:3738–3746 (1988).
Heinzel, S.S. et al., "Autonomous DNA Replication in Human Cells is Affected by the Size and Source of the DNA," Mol. and Cel. Biol. 11:4:2261–2272 (1991).
Higgins, K. A., et al., "Antisense inhibition of the p65 subunit of NF–$_\kappa$B blocks tumorigenicity and causes tumor regression," Proc. Natl. Acad. Sci. 90:9901–9905 (1993).
Higgins, C.F. et al., "Cystic fibrosis mice have arrived!" Human Molec. Genetics 1:7:459–460 (1992).
Hyde, S.C. et al., "Correction of the ion transport defect in cystic fibrosis transgenic mice by gene therapy," Nature 362:250–255 (1993).
Krysan, P.J. et al., "Replication Initiates at Multiple Locations on an Autonomously Replicating Plasmid in Human Cells," Molec. and Cel. Biol. 11:3:1464–1472 (1991).
Krysan, P.J. et al., "Isolation of Human Sequences that Replicate Autonomously in Human Cells," Molec. and Cel. Biol. 9:3:1026–0133 (1989).
Krysan, P.J. et al., "Autonomous Replicatin in Human Cells of Multimers of Specific Human and Bacterial DNA Sequences," Molec. and Cel. Biol. 13:5:2688–2696 (1993).
Krysan, P.J. et al., "Epstein–Barr virus–based vectors that replicate in rodent cells," Gene 136:137–143 (1993).

(List continued on next page.)

Primary Examiner—David Guzo
Attorney, Agent, or Firm—Charles K. Sholtz; Gary R. Fabian; Peter J. Dehlinger

[57] ABSTRACT

The present invention describes an expression vector useful for transfection of a selected mammalian host cell. The vector includes the following components: an Epstein Barr Virus (EBV) family of repeats; a copy of the EBV Nuclear Antigen-1 (EBNA-1) gene that can be functionally expressed in the host cell; a eucaryotic DNA fragment, which provides the ability of the vector to replicate in host cells; and an expression cassette which comprises a promoter functional in said host cell, a coding sequence having 5' and 3' ends, where said coding sequence is functionally linked to said promoter, where said 5' end is adjacent the promoter and said 3' end is adjacent transcription termination sequences. The vector of the present invention is useful in the transfection of mammalian cells, including rodent and human cells. The vector is stably retained and replicates in concert with genomic sequences of the host cell, that is, the vector is typically replicated once per cell cycle. The vector is useful in the follow methods involving mammalian cells: producing proteins, stable transformation, and gene therapy.

24 Claims, 12 Drawing Sheets

OTHER PUBLICATIONS

Lebkowski, J.S. et al., "Transfected DNA Is Mutated in Monkey, Mouse, and Human Cells," Molec. and Cel. Biol. 4:10:1951–1960 (1984).

Lupton, S. et al., "Mapping Genetic Elements of Epstein–Barr Virus that Facilitate Extrachromosomal Persistence of Epstein–Barr Virus–Derived Plasmids in Human Cells," Molec. and Cel. Biol. 5:10:2533–2542 (1985).

Margolskee, R. F., et al., "Epstein–Barr Virus Shuttle Vector for Stable Episomal Replication of cDNA Expression Libraries in Human Cells," Molec. & Cell. Biol. 8:7:2837–2847 (1988).

Miller, A. D., "Human gene therapy comes of age," Nature 357:455–460 (1992).

Mulligan, R.C., "The Basic Science of Gene Therapy," Science 260:926–932 (1993).

Peterson, C. et al., "High–frequency transformation of human repair–deficient cell lines by an Epstein–Barr virus–based cDNA expression vector," Gene 107:279–284 (1991).

Ravnan, J–B, et al., "Random–Choice Replication of Extrachromosomal Bovine Papillomavirus (BPV) Molecules in Heterogeneous, Clonally Derived BPV–Infected Cell Lines," J. Virol. 66:12:6946–6952 (1992).

Reisman, D., et al., "A Putative Origin of Replication of Plasmids Derived from Epstein–Barr Virus Is Composes of Two cis–Acting Components," Molec. and Cel. Biol. 5:8:1822–1832 (1985).

Tran, C.T. et al., "The replication behavior of *Saccharomyces cerevisiae* DNA in human cells," Chromosoma 102:129–136 (1993).

Yates, J. et al., "A *cis*–acting element from the Epstein–Barr viral genome that permits stable replication of recombinant plasmids in latently infected cells," Proc. Natl. Acad. Sci. 81:3806–3810 (1984).

Yates, J.L. et al., "Stable replication of plasmids derived from Epstein–Barr virus in various mammalian cells," Nature 313:28:812–815 (1985).

Yates, J.L., et al., "Epstein–Barr Virus–Derived Plasmids Replicate Only Once per Cell Cycle and are not Amplified after Entry into Cells," J. Virol. 65:1:483–488 (1991)..

Young, J. M. et al., "Utilization of an Epstein–Barr virus replicon as a eukaryotic expression vector," Gene 62:171–185 (1988).

Fig. 3A
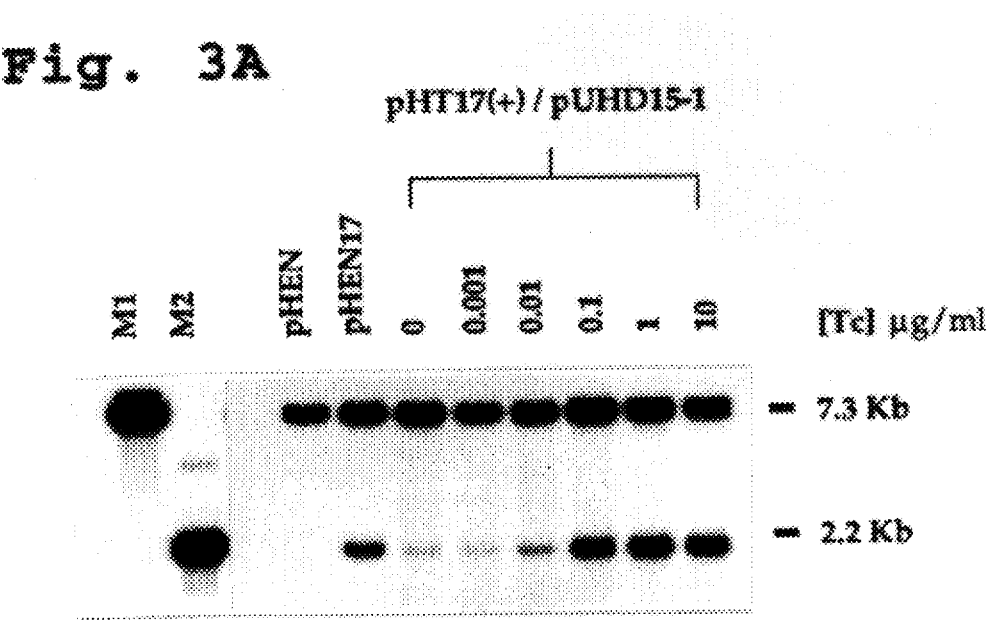
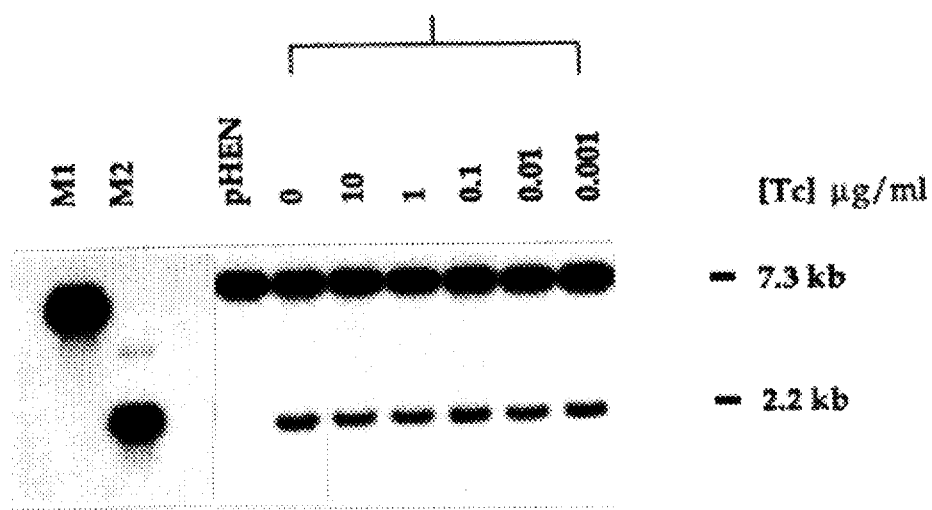
Fig. 3B

| SOURCE | PRODUCT VECTOR |
|---|---|
| pML + 2 identical λ fragments | pMLλ |
| pMLλ + Not I sites | pNUT |
| pNUT + human fragment 17 (H17) | pH17 |
| pH17 + human fragment 2 or human fragment 4 | pH172 and pH174 |
| pMLλ, exchange 156 bp fragment with pNUT to gain NotI site | pHEN |
| pHEN + H17 | pHEN17 |
| pHEN17 + UMS | pHEN17U |
| pHEN17U + CMV promoter, both orientations + H17 | pHC17(-) and pHC17(+) |
| pHEN + UMS | pHENU |
| pHEN + CMV promoter, both orientations + UMS + H17 | pHUC17(+) and pHUC17(-) |
| pHEN + β-actin promoter, both orientations | pHBA(+) and pHBA(-) |
| pHBA(+) and pHBA(-) + H17 | pHB17 (+) and pHB17(-) |
| pHEN + tetracycline-responsive promoter, both orientations, + H17 | pHT17(+) and pHT17(-) |
| pBODY + H17 | pBODY17 |
| pBODY + CMV promoter, both orientations + H17 | pBC17(+) and pBC17(-) |
| pBODY + CMV promoter, both orientations + UMS + H17 | pBUC17(+) and pBUC17(-) |

Fig. 10

AUTONOMOUS REPLICATON SYSTEM FOR MAMMALIAN CELLS

This application is a file-wrapper-continuation of application Ser. No. 08/246,867, filed May 20, 1994, now abandoned.

This invention was made with Government support under contract RO1 CA33056 awarded by the National Cancer Institute. Accordingly, the United States Government has certain rights in this invention.

FIELD OF THE INVENTION

The autonomously replicating vectors of the present invention are useful for the stable transformation of mammalian cells, including human and rodent cells, and for use in gene therapy applications.

REFERENCES

Acsadi, G., et al., NATURE 352:815 (1991).

Adams, A., J. VIROL. 61:1743–1746 (1987).

Agrawal, S., et al., PROC. NATL. ACAD. SCI. USA 86:7790–7794 (1989).

Alton, E. W. NATURE GENETICS 5:135–142 (1993).

Anderson, W. F. SCIENCE 256:808–813 (1992).

Ashman, C. R., et al., SOMATIC CELL MOL. GENET. 11:499–504 (1985).

Ausubel, F. M., et al., *CURRENT PROTOCOLS IN MOLECULAR BIOLOGY*, John Wiley and Sons, Inc., Media Pa.

Baer, R., et al., NATURE 310:207–211 (1984).

Behrend, E. I., et al., CANCER RES. 54(3):832–837 (1994).

Belt, P. B. G. M., et al., GENE 84:407–417 (1989).

Berns, A. J. M., U.S. Pat. No. 5,174,986, issued 29 Dec. 1992.

Boshart, M., et al., CELL 41:521–530 (1985).

Brewer, B. J., et al., CELL 51:463–471.

Brigham, K. L., et al., AM. J. MED. SCI. 298:278 (1989).

Caddle, M. S., J. MOL. BIOL. 211:19–33 (1990).

Castanotto, D., et al., CRITICAL REVIEWS IN EUKARYOTIC GENE EXPRESSION 2(4):331–357 (1992).

Coutelle, C., et al., ARCH. DIS. CHILD. 68(4):437–440 (1993).

Cristiano, R. J., et al., PROC. NATL. ACAD. SCI. USA 90:11548–11552 (1993).

Debs, R., et al., J. BIO. CHEM. 265:10189 (1990).

Debs, R., et al., AM. J. RESPIR. CELL MOL. BIOL. 7:406 (1992).

Drinkwater, N. R., et al., PROC. NATL. ACAD. SCI. USA 83: 3402–3406 (1986).

Dropulic, B., et al., ANTISENSE RESEARCH AND DEVELOPMENT 3(1):87–94 (1993).

DuBridge, R. B., et al., MOL. CELL. BIOL. 7:379–387 (1987).

DuBridge, R. B., et al., MUTAGENESIS 3:1–9 (1988).

Feinstein, S. C., et al., J. MOL. BIOL. 156:549 (1982).

Felgner, P., et al., PROC. NATL. ACAD. SCI. U.S.A. 84:7413 (1987).

Fiering, S. N., et al., CYTOMETRY 12:291–301 (1991).

Fujita, M., et al., FEBS LETT. 322(1):15–20 (1993).

Gilbert, D. M., et al., CELL 50:59–68 (1987).

Gorman, C. M., et al., PROC. NATL. ACAD. SCI. USA 79:6777 (1982).

Gossen, M., et al., PROC. NATL. ACAD. SCI. USA 89:5547–5551 (1992).

Gussoni, E., et al., NATURE 356: 435–438 (1992).

Haase, S. B., et al., Nuc. ACIDS RES. 19:5053–5058 (1991).

Harris, A., et al., J. VIROL. 56:328–332 (1985).

Heard, J., et al., MOL. CELL. BIOL. 7:2425–2434 (1987).

Heinzel, S. S., et al., J. VIROL. 62:3738–3746 (1988).

Heinzel, S. S., et al., MOL. CELL. BIOL. 11:2263–2271 (1991).

Higgins, C. F., et al., HUM. MOL. GENET. 1(7):459–460 (1992).

Higgins, K. A., et al., PROC. NATL. ACAD. SCI. USA 90:9901–9905 (1993).

Hirt, B. J. MOL. BIOL. 26:365–369 (1967).

Hogan, B., et al., *MANIPULATING THE MOUSE EMBRYO*, Cold Spring Harbor Press, Cold Spring Harbor, N.Y. (1986).

Hyde, S. C., et al., NATURE 362(6417):250–255 (1993).

Johnson, H. M., et al., SCIENTIFIC AMERICAN 270(5):68–75 (1994).

Kay, M. A., et al., PROC. NATL. ACAD. SCI. USA 91(6):2353–7 (1994).

Krysan, P. J., et al., MOL. CELL. BIOL. 9:1026–1033 (1989).

Krysan, P. J., et al., MOL. CELL. BIOL. 11:1464–1472 (1991).

Krysan, P. J., et al., MOL. CELL. BIOL. 13:2688–2696 (1993).

Lebkowski, J. S., et al., MOL. CELL. BIOL. 4:1951–1960 (1984).

Lewalle, P., et al., LEUK. LYMPHOMA. 11(Suppl 1):139–143 (1993).

Lo, K. M., et al., VIROLOGY 190(1):176–183 (1992).

Lupton, S., et al., MOL. CELL. BIOL. 5:2533–2542 (1985).

MacDonald, R. J., et al., p. 219–227, *GUIDE TO MOLECULAR CLONING TECHNIQUES*, eds. S. L. Berger and A. R. Kimmel, Academic Press Inc., San Diego (1987).

McGeady, M. L., et al., DNA 5:289–298 (1986).

Maniatis, T., et al., *MOLECULAR CLONING: A LABORATORY MANUAL*, Cold Spring Harbor Laboratory (1982).

Margolskee, R. F., et al., MOL. CELL. BIOL. 8:2837–2847 (1988).

Matsukura, M., et al., PROC. NATL. ACAD. SCI. USA 86:4244–4248 (1989).

Miller, A. D. NATURE 357:455–460 (1992).

Mulligan, R. C., SCIENCE 260:926–932 (1993).

Mullis, K. B., U.S. Pat. No. 4,683,202, issued 28 Jul. 1987.

Mullis, K. B., et al., U.S. Pat. No. 4,683,195, issued 28 Jul. 1987.

Nolan, G. P., et al., PROC. NATL. ACAD. SCI. U.S.A. 85:2603–2607.

Ng, S. Y., et al., MOL. CELL. BIOL. 5:2720–2732 (1985). Perlakey, L., et al., ANTI-CANCER DRUG DESIGN 8:3–14 (1993).

Peterson, C., et al., GENE 107:279–284 (1991).

Philip, R., et al., J. BIOL. CHEM. 268:16087–16090.

Pursell, V. G., et al., SCIENCE 244:1281–1289.

Ratajczak, M. Z., et al., PROC. NATL. ACAD. SCI. USA 89:8474–8478 (1992).

Ravnan, J.-B., et al., J. VIROL. 66:6946–6952 (1992).

Rawlins, D. R., et al., CELL 42:859–868 (1985).

Reisman, D., et al., MOL. CELL. BIOL. 5:1822–1832 (1985).

Riordan, J. R., et al., SCIENCE 245:1066–1073 (1989).

Rittner, K., et al., NUCLEIC ACIDS RES. 19:1421–1426, (1991).

Sambrook, J., et al., In MOLECULAR CLONING: A LABORATORY MANUAL, Cold Spring Harbor Laboratory Press, Vol. 2 (1989).

Salier, J., et al., BIOTECHNIQUES 7:30–31 (1989).

Smith, C. A., J. AM. VET. MED. ASSOC. 204(1):41–46 (1994).

Stein, C. A. and Cheng, Y.-C., SCIENCE 261:1004–1012 (1993).

Stillman, B. W., et al., MOL. CELL. BIOL. 5:2051–2060 (1985).

Stribling, R., et al., PROC. NATL. ACAD. SCI. USA 89:11277–11281 (1992).

Sugden, B., et al., MOL. CELL. BIOL. 5:410–413 (1985).

Sugden, W. M., U.S. Pat. No. 4,686,186, issued 11 Aug. 1987.

Szybalski, W., METH. ENZYMOL. 12:330–360 (1968).

Taylor, N. R., et al., NUCL. ACIDS RES. 20(17):4–559–4565 (1992).

Thomsen, D. R., et al., PROC. NATL. ACAD. SCI. USA 81:659–663 (1984).

Tran, C. T., et al., CHROMOSOMA 102:129–136 (1993).

Wigler, M., R. et al., CELL 16:777–785 (1979).

Yates, J., et al., PROC. NATL. ACAD. SCI. USA 81:3806–3810 (1984).

Yates, J. L., et al., NATURE (LONDON) 313:812–815 (1985).

Yates, J. L., et al., J. VIROLOGY 65:483–488 (1991).

Young, J. M., et al., GENE 62:171–185 (1988).

Zamecnik, P. C., et al., PROC. NATL. ACAD. SCI. USA 83:4143–4146 (1986).

Zhang, Y., et al., HUMAN GENE THER. 4(4):451–460 (1993).

Zhu, N., et al., SCIENCE 261:209–211 (1993).

BACKGROUND OF THE INVENTION

The field of gene therapy is in its infancy, but holds great promise for therapy of cancer and other genetically based diseases (Anderson, 1992; Miller, 1992; Mulligan, 1993). Current approaches focus on using viral vectors to deliver genes. However, these vectors have important inherent limitations including restricted size capacity, risk of creating mutations upon integration, immunogenicity of viral proteins, and difficulty of preparation (Mulligan, 1993).

In the past few years many animal models, particularly rodent models, have been developed for human diseases—including several genetic diseases amenable to gene therapy (e.g., Higgins, et al., 1992; Coutelle, et al., 1993; Hyde, et al., 1993). Extrachromosomal vectors that replicate stably and are retained in cells over the long-term have been unavailable for rodent cells. Vectors based on lytic viruses such as polyoma are useful for short-term experiments, but they are unstable, replicate many times per cell cycle, and are not suitable for long-term experiments (Lebkowski, et al., 1984). Vectors based on bovine papilloma virus do not consistently replicate once per cell cycle (Gilbert, et al., 1987; Ravnan, et al., 1992), and they show a high frequency of rearrangements (Ashman, et al., 1985; DuBridge, et al., 1988).

In human and other primate cells, vectors based on Epstein-Barr virus (EBV) (Yates, et al., 1984; Reisman, et al., 1985; Lupton, et al., 1985) do replicate once per cell cycle (Adams, 1987; Yates, et al., 1991; Haase, et al., 1991) and are stably maintained over the long-term with a very low mutation frequency (DuBridge, et al., 1987; Drinkwater, et al., 1986). These vectors have been used for cloning and expression studies in human and simian cells (Margolskee, et al., 1988; Young, et al., 1988; Belt, et al., 1989; Peterson, et al., 1991). Stable transformation frequencies are high since integration into the genome is not required, and recovery of cloned sequences can be achieved by simple plasmid extraction. However, rodent cells are not permissive for EBV replication, and no rodent counterpart of EBV has been described (Yates, et al., 1985).

Recently, efficient methods of delivering DNA-liposome complexes to tissues have been described (Alton, et al., 1993; Hyde, et al., 1993; Philip, et al., 1993; Stribling, et al., 1992; Zhu, et al., 1993).

SUMMARY OF THE INVENTION

The present invention relates to vectors and their methods of use. In one embodiment, the present invention includes a vector composition comprising an expression vector useful for transfection of a host cell. The host cell is typically a mammalian cell, for example, human, primate, sheep, pig or rodent. The vector of the present invention includes an Epstein Barr Virus (EBV) family of repeats and a copy of the EBV Nuclear Antigen-1 (EBNA-1) gene that can be functionally expressed in the host cell.

In addition, the vector contains a large fragment of DNA, which provides the ability of the vector to replicate in host cells. The DNA fragment is typically derived from eucaryotes (for example, human or yeast sequences), but may also be obtained from other sources (such as procaryotes). In one embodiment, the DNA fragments are randomly generated fragments of human genomic DNA. The size of the fragments is usually between approximately 8 and approximately 20 kilobases (kb). DNA fragments for use in the vector and methods of the present invention can be screened for their ability to facilitate replication of the vector by the methods described herein.

The vector of the present invention also includes an expression cassette which comprises a promoter that is functional in the host cell, a coding sequence operably linked to the promoter. Transcription from the expression cassette promoter is terminated by transcription termination sequences, typically placed at the 3' end of the gene. The function of the transcription termination sequences is essentially to prevent read-through transcription from the expression cassette promoter, particularly to prevent transcription through the region of the plasmid containing the large DNA fragment described above. A vector of the present invention can contain one or more expression cassettes.

The coding sequence of the expression cassette can contain any nucleic acid sequence of interest. In one embodiment, the coding sequence is a gene encoding a gene product useful for genetic selection in the host cell (for example, a gene conferring hygromycin or neomycin resistance). In another embodiment, the coding sequence is a reporter gene, encoding, for example, chloramphenicol acetyl transferase, β-galactosidase, or luciferase. Further, the coding sequences in the expression cassette can encode any products useful in gene therapy applications, such as, polypeptides, antisense RNA and ribozymes.

Numerous promoters (e.g., cytomegalovirus, SV40, or MMTV-LTR) and transcription termination sequences (e.g., upstream mouse sequences (UMS), SV40, or Herpes Simplex Virus I transcription termination sequences) useful in the construction of vectors of the present invention are known in the art. In one embodiment of the invention, the expression cassette promoter is a cytomegalovirus promoter and the transcription termination sequences are UMS. The effects of pairs of promoters and transcription termination sequences on vector stability and replication can be evaluated as described herein. One or more transcription termination region may be used to effectively terminate transcription.

The vectors of the present invention may also include DNA sequences that allow the propagation of the vector in a secondary host, such as, sequences containing an origin of replication and a selectable marker. Typical secondary hosts include bacteria and yeast. In one embodiment, the secondary host is *Escherichia coli*, the origin of replication is a colE1-type, and the selectable marker is a gene encoding ampicillin resistance.

The present invention also includes cells transformed with the above described vectors. Further, the present invention includes a method for expression of a protein in cells (e.g., mammalian cells) which includes transfecting a host cell with a vector (described above), and culturing the transfected cells under suitable conditions so that the polypeptide is produced by the cells. In another embodiment, the invention includes a method of isolating the polypeptides expressed by transfected cells.

A further embodiment of the present invention includes a method of maintaining stably transformed cells (e.g., mammalian cells). In this method, a host cell or cell-type is selected. An expression vector is prepared as described above. The expression vector is introduced into the host cell, and the host cell into which said expression vector has been introduced is maintained. Such transfected cells include dividing and non-dividing cells and can be maintained in vitro or in vivo. The host cells may be, for example, human, primate, sheep, pig or rodent.

The present invention also includes gene therapy applications (including human and veterinary) using the vectors of the present invention. One embodiment of the invention is a method for remedying genetic defects in target cells. Such defects include disease states caused by viral infection or inappropriate expression of cellular genes (e.g., deficiencies and over-expression). In this method, an expression vector is prepared as described above. The expression vector is then introduced into the target cell. The target cells may be in a living animal (for example, lung cells) or cells that are maintained in vitro that will be re-introduced into a host animal. The expression cassette coding sequences may encode, but are not limited to, the following products: polypeptides, antisense RNA or ribozymes. In one embodiment, the genetic defect is in the gene for the cystic fibrosis transmembrane regulator protein and the coding sequence encodes a functional cystic fibrosis transmembrane regulator protein. In this embodiment the vector can be administered by inhalation, typically, in complexes with lipids.

The present invention also includes pharmaceutical compositions of the above described vectors.

These and other objects and features of the invention will be more fully appreciated when the following detailed description of the invention is read in conjunction with the accompanying drawings.

BRIEF DESCRIPTION OF THE FIGURES

FIGS. 3A, 3B and 3C present data demonstrating replication activity of plasmids containing the tetracycline-responsive promoter correlates with the level of tetracycline in the media. FIG. 3C shows a graph of the data presented in A. Bands were quantitated by laser densitometry.

FIG. 9A shows hybridization analysis using $^{32}$P-labeled pDY⁻ plasmid as a probe. FIG. 9B shows hybridization analysis using a labeled fragment of hamster genomic DNA which contains a copy of the hamster Alu repeat as a probe.

FIG. 10 presents a summary of the plasmid constructions described in Example 1.

DETAILED DESCRIPTION OF THE INVENTION

Figure 1A:
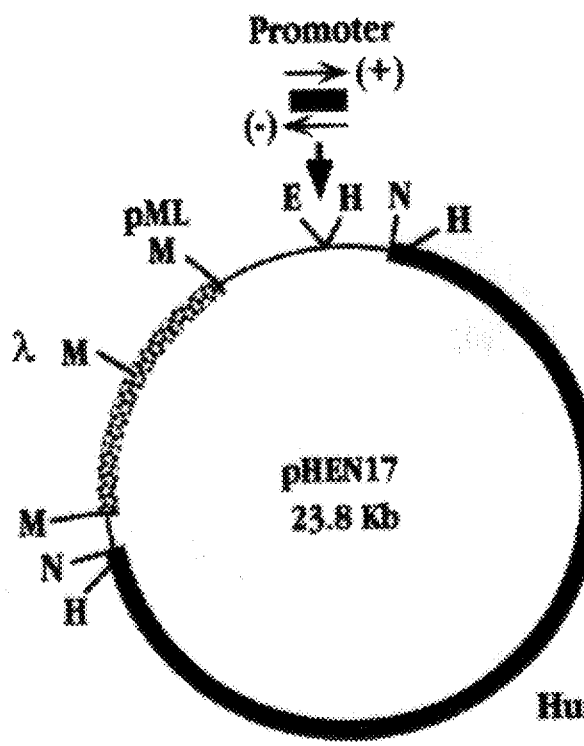
FIG. 1A presents a map of the plasmid pHEN17.

I. INHIBITION OF THE REPLICATION OF AUTONOMOUSLY REPLICATING PLASMIDS IN HUMAN CELLS BY TRANSCRIPTION.

Experiments performed in support of the present invention have demonstrated that sequences from the Epstein-Barr virus (EBV) genome could provide a nuclear retention function (Krysan, et al., 1989). Plasmids containing the family of repeats from the EBV latent origin of replication, oriP, are retained stably in the nuclei of human cells which express the EBV EBNA-1 gene, even in the absence of the EBV replication function provided by a region of dyad symmetry (Krysan, et al., 1989). Human genomic sequences cloned on plasmids containing nuclear retention sequences were shown to replicate stably in human cells (Krysan, et al., 1989). These human sequences also mediated replication in the absence of any EBV sequences in a short term replication assay (Heinzel, et al., 1991; Krysan, et al., 1989).

A collection of random human fragments of varying sizes, revealed that a broad range of human DNA fragments were capable of replication in both short and long-term assays and that replication efficiency was positively correlated with the size of the human DNA fragment (Heinzel, et al., 1991). Using a two-dimensional gel analysis of replication products (Brewer, et al., 1987), replication was shown to initiate at many sites on a plasmid carrying a 20 kb human fragment (Krysan, et al., 1991). These findings are consistent with the idea that there is little sequence specificity required to initiate replication in human cells.

A density shift analysis of several plasmids replicating by virtue of human sequences confirmed that the plasmids were replicating semi-conservatively and with an efficiency comparable to that of the chromosome (Haase, et al., 1991). This analysis also showed that these plasmids were subject to once per cell cycle control.

The interaction between (i) transcriptional elements, and (ii) sequences required for replication initiation on autonomously replicating vectors, was evaluated as follows.

A. EFFECT OF THE CMV PROMOTER/ENHANCER AND THE HUMAN B-ACTIN PROMOTER ON THE REPLICATION ACTIVITY OF AN AUTONOMOUSLY REPLICATING PLASMID.

Human fragment 17 has been shown to promote replication of a prokaryotic vector (Heinzel, et al., 1991) in a short-term replication assay using 293S cells (Krysan, et al., 1989). The plasmid pHEN17 (Example 1) contains the 17 kb human fragment cloned into the prokaryotic vector, pHEN (Example 1, FIG. 10). The plasmid pHEN served as the negative replication control.

Two plasmids, pHC17(+) and pHC17(−) (FIG. 1A), were constructed that contain the human cytomegalovirus (CMV) promoter/enhancer (Boshart, et al., 1985) in both orientations in the HindIII site of pHEN17. The human β-actin promoter (Ng, et al., 1985), a strong promoter that is active in a variety of cell lines, was used to create pHB17(+) and pHB17(−). These plasmids contain the β-actin promoter located in an EcoRI site, as well as the human fragment 17 and the pHEN backbone sequences (Example 1).

Approximately equimolar amounts of these plasmids were transfected into a human embryonic kidney cell line, 293S (Stillman, et al., 1985), and assayed for replication activity (Example 2). After 4 days in culture, transfected cells were Hirt extracted in order to isolate low molecular weight DNA (Hirt, 1967).

Figure 1B:
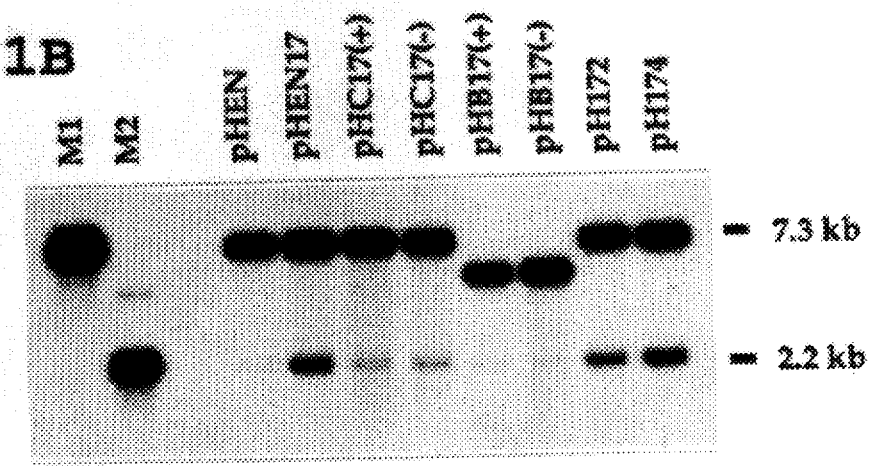
FIGS. 1B, 1C and 1D present the results of DNA hybridization analysis of MboI/HindIII digested (FIG. 1B), undigested (FIG. 1C) and DpnI digested (FIG. 1D) Hirt extracts taken four days post-transfection. The data demonstrate the inhibition of plasmid replication by promoter elements.

The results of a typical replication assay using the above plasmids is shown in FIG. 1B. Essentially no replication was detected for the negative control plasmid, pHEN (FIG. 1B). The 7.4 kb band represents DNA that was not digested by MboI and thus has replicated once or not at all in the target cells. Plasmid replication was readily detectable for the positive control, pHEN17 (FIG. 1B). The 2.2 kb MboI band represents DNA that has replicated at least twice.

Replication activities were substantially reduced of plasmids that contained the (i) CMV or (ii) β-actin promoter elements, in either orientation, when compared to pHEN17 (FIG. 1B). Plasmids pHC17(+) and pHC17(−) showed approximately 5-fold reductions in replication activity. Plasmids pHB17(+) and pHB17(−) showed approximately 10-fold reductions in replication activity (i.e., reduced levels of MboI sensitive DNA).

The replication activities of the two plasmids pH172 and pH174 (Example 4) were similar to the activity of pHEN17.

These vectors each contained a randomly isolated human genomic fragment (2 kb and 4 kb, respectively) cloned into pH17. The replication results obtained with these two vectors suggests that the addition of DNA sequences to the HindIII site of pH17 does not have a negative effect on the replication of the plasmid.

Figure 1C:
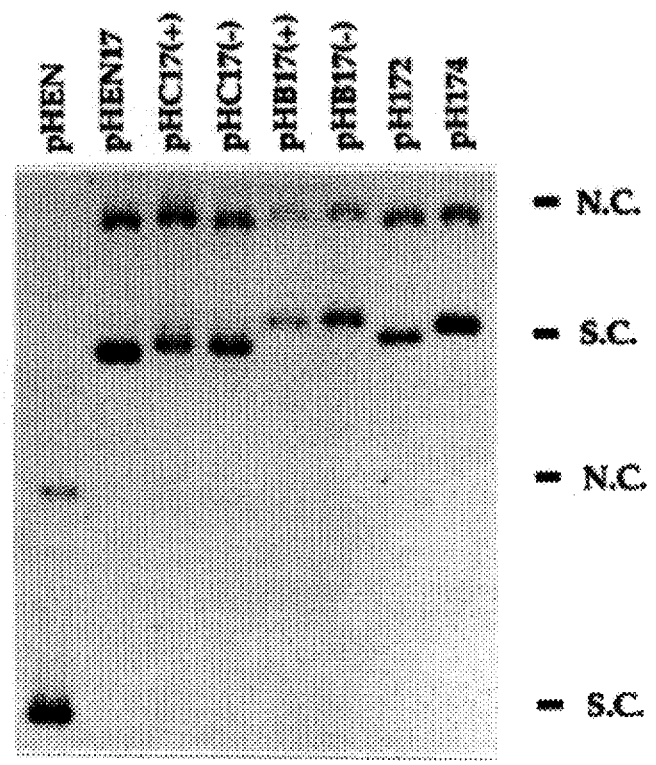

Results confirming that the plasmids were being maintained extrachromosomally are shown in FIG. 1C. The results demonstrate that all of the plasmids ran as super-coiled and nicked circles, indicating that they were predominantly extrachromosomal.

Figure 1D:
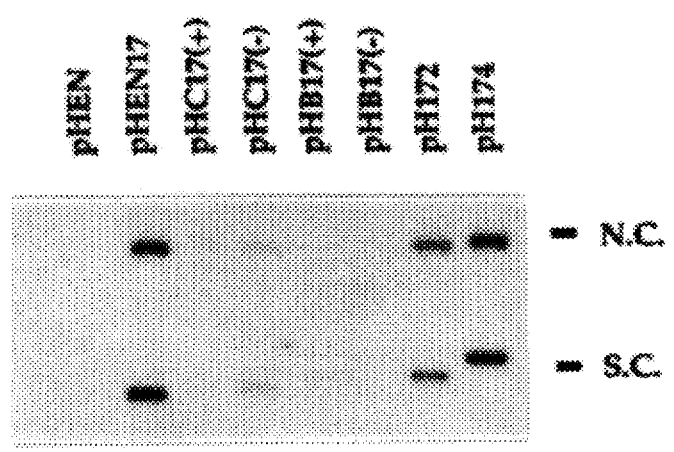

The results presented in FIG. 1D confirm that the replication activity observed in the above described experiments was occurring on autonomous plasmids. DNA samples isolated from the cells containing the vectors shown in FIG. 1D were digested with the restriction endonuclease DpnI. Cleavage of DNA by this restriction endonuclease is dependent on methylation, i.e., it will only digest DNA produced in bacteria having a bacterial methylation pattern. Accordingly, if DNA has replicated 1 or more times in human cells it is not sensitive to digestion.

Plasmid DNA that replicated in human cells and was not digested by DpnI ran as super-coiled and nicked circles (FIG. 1D). The results obtained by this analysis provide confirmation of the results shown in FIG. 1B above. Replicated DNA was readily detectable for pHEN17, pH172 and pH174. Replication activity of the negative control, pHEN, and the plasmids containing promoter elements, pHC17(+), pHC17(−), pHB17(+) and pHB17(−), was reduced.

The data presented above also confirmed that these plasmids were replicating as autonomous plasmids, since there was no evidence in the DNA hybridization analyses of integration of the vector sequences into the cellular genomes.

Further, the data demonstrate that the addition of promoter elements to autonomously replicating plasmids based on human sequences interferes with plasmid replication. Both the CMV and human β-actin promoters inhibited the replication of autonomous plasmids.

B. CONDITIONAL INHIBITION OF REPLICATION BY AN INDUCIBLE PROMOTER.

The effects of promoter activity were separated from potential cis-acting effects of the promoter sequences on replication activity as follows. The effects of an inducible promoter on the replication of autonomous plasmids was evaluated. The tetracycline-responsive promoter system was selected (Gossen, et al., 1992).

The tetracycline-responsive promoter is transcriptionally inactive until induced by the presence of a transcriptional transactivator protein (tTA). The activity of the tetracycline-responsive promoter can be negatively modulated by the presence of tetracycline in the growth media. Increasing levels of tetracycline quantitatively reduce the level of expression from the tetracycline-responsive promoter in the presence of tTA (Gossen, et al., 1992).

Figure 2:
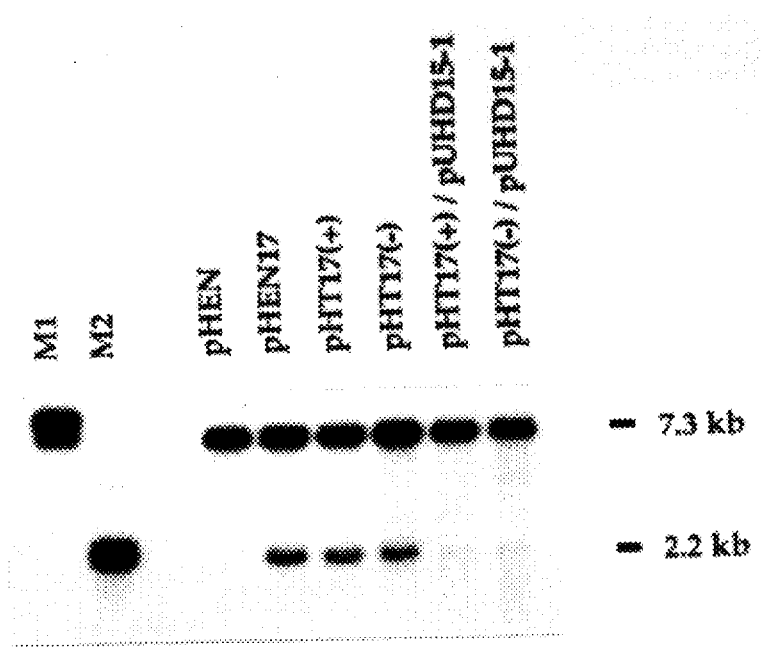
FIG. 2 presents DNA hybridization data demonstrating conditional inhibition of plasmid replication by the tetracycline-responsive promoter.

Experiments performed in support of the present invention demonstrate that plasmid replication could be conditionally inhibited by the tetracycline-responsive promoter (Example 5). In the inactive state, the tetracycline-responsive promoter had no effect on replication activity. However, when promoter activity was induced by providing tTA (Gossen, et al., 1992), plasmid replication was inhibited (FIG. 2).

Furthermore, the addition of tetracycline to the growth media, which has been shown to quantitatively down regulate the promoter, restored plasmid replication activity (Example 6). The level of replication activity was positively correlated with the concentration of tetracycline in the media (FIGS. 3A and 3C).

As a control for the possibility of direct effects of tetracycline on the replication activity of autonomous plasmids, a vector that contained no tetracycline-responsive promoter sequences, pHEN17, was co-transfected with the tTA expression vector, pUHD15-1 (Example 6). The assayed replication activity was then evaluated for varying levels of tetracycline. The data presented in FIG. 3B demonstrate that tetracycline had no significant effect on the replication activity of the plasmid pHEN17.

These findings suggest that the inhibition of plasmid replication is due to promoter activity and that the level of replication inhibition is related to the level of promoter activity.

C. THE INHIBITION OF PLASMID REPLICATION IS RELATED TO TRANSCRIPTION.

In view of the results obtained from the above experiments, promoter elements have two functions that could potentially interfere with plasmid replication. Replication may be inhibited by (i) proteins binding to promoter elements, or (ii) transcription function directed by promoter elements. Further experiments performed in support of the present invention demonstrated that transcription functions are responsible for the inhibition of replication.

The plasmid, pBODY17, contains the human fragment 17 used in the experiments above, as well as sequences from the Epstein-Barr virus (EBV) that have been shown to provide nuclear retention (Krysan, et al., 1989; Heinzel, et al., 1991). The plasmid also contains an active transcription unit composed of the promoter from the herpes simplex type 1 thymidine kinase gene driving the expression of the hygromycin resistance gene. The thymidine kinase transcriptional terminator is located at the end of the hygromycin resistance gene (Sugden, et al., 1985).

Figure 4A:
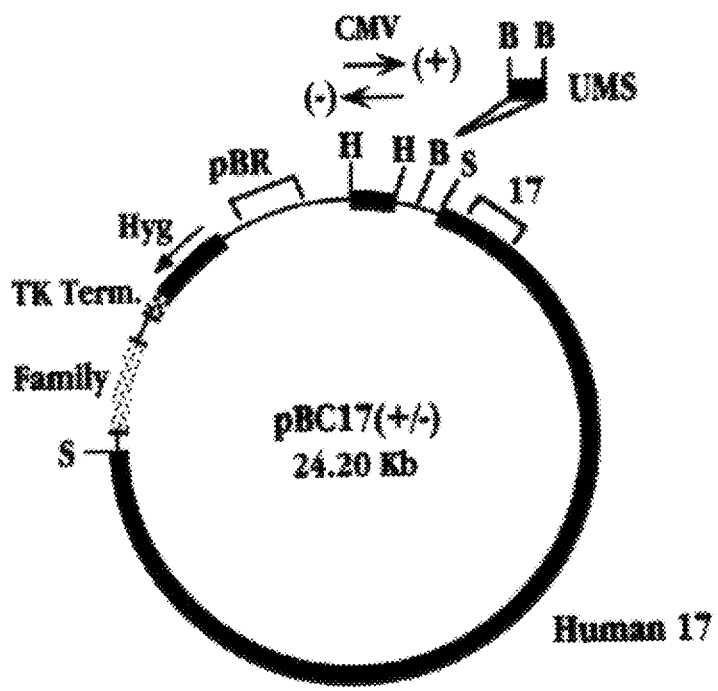
FIG. 4A shows a map of plasmids pBC17(+)/pBC17(−).
Figure 4B:
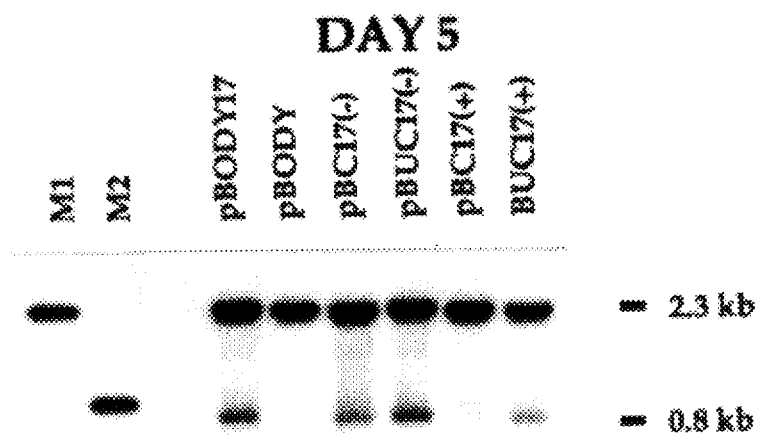
FIGS. 4B and 4C present data demonstrating promoter orientation dependent replication and transcription termination.
Figure 4C:
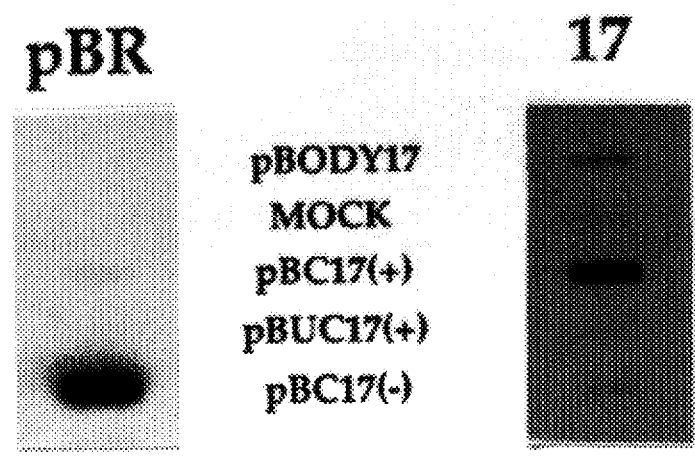

The CMV promoter inhibited the replication of a pBODY17 plasmid in only one promoter orientation (Example 7, FIGS. 4B and 4C). When the UMS terminator was cloned into pHEN17, the CMV promoter inhibited the replication of pHEN17 plasmid in only one orientation (Example 8, FIG. 5). The observation that replication inhibition is dependent on the orientation of promoter sequences is not consistent with hypothesis that protein binding is responsible for the inhibition of plasmid replication.

Paired plasmids were also generated that were identical except that they contained the CMV promoter in opposite orientations (FIG. 4A). Derivatives of these plasmids were generated that had the upstream mouse sequence (UMS; shown to efficiently terminate transcription in mammalian cells; Heard, et al., 1987; McGeady, et al., 1986; Salier, et al., 1989) cloned adjacent to the CMV promoter (FIG. 4A). Plasmid pBUC17(+) has the UMS placed downstream of the promoter. Plasmid pBUC17(−) has the UMS located upstream of the promoter.

Replication studies were carried out with these vectors. The data presented in FIG. 4B demonstrate that the positive control, pBODY17, showed strong replication while the negative control, pBODY, showed little replication activity. The plasmids containing the CMV promoter element showed an inhibition of replication in an orientation-dependent manner (pBC17(+), FIG. 4B, reduced compared to pBODY17; pBC17(−), little or no replication inhibition). In plasmid pBC17(−), transcription from the CMV promoter proceeded in the same direction as transcription from the hygromycin resistance gene, which has a putative transcription termination sequence at the 3' end of the expression unit.

Further, the results presented in FIG. 4B (Example 7) demonstrate that a transcriptional terminator can mitigate the inhibition of replication by promoter elements, suggesting that transcription is directly involved in the inhibition of plasmid replication. For example, the replication activity of pBUC17(+) was 7-fold more than pBC17(+); pBC17(+) contains no transcription terminator sequences (FIG. 4B).

These results support the conclusion that the orientation effect observed in pBODY was likely related to the termination of transcription by the thymidine kinase (TK) terminator. The transcription termination hypothesis is further supported by data demonstrating that the UMS could restore most of the replication activity of a pHEN17 plasmid containing a CMV promoter when it was placed downstream of the promoter sequences (pHEN17(−); Example 8, FIG. 5), but not when placed upstream of the promoter sequences (pHEN17(+), FIG. 5).

These results support the idea that the orientation effect seen in pBODY17 plasmids is a result of transcription termination. Therefore, the UMS, which has been shown to function as a transcription terminator, affects replication activity when placed downstream but not upstream of promoter sequences. These data strongly suggest that transcription and not protein binding are responsible for the inhibition of plasmid replication.

The UMS sequence was not able to completely restore replication activity to plasmids containing the CMV promoter, compared to control plasmids without promoter elements. It is possible that the UMS element does not completely terminate transcription or that a mechanism in addition to transcription is also inhibiting replication.

Figure 5:
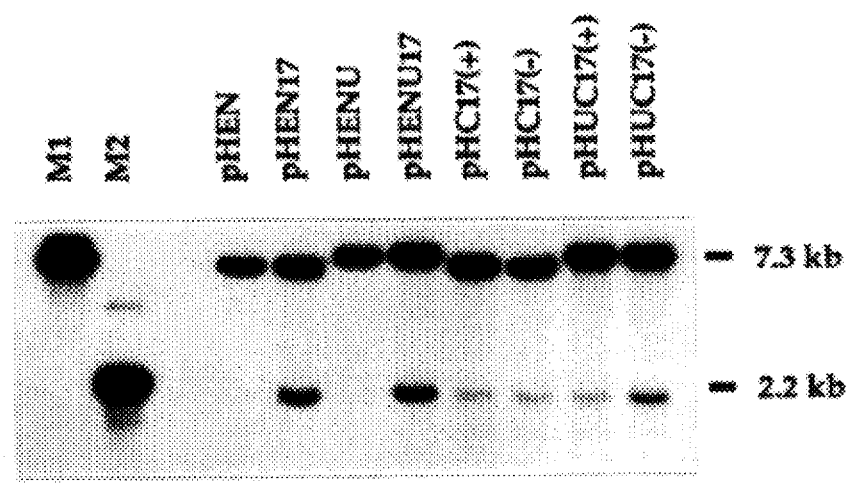
FIG. 5 shows data demonstrating the mitigation of replication inhibition by the transcription termination sequences (UMS).

The orientation dependent inhibition of replication observed in plasmids containing transcription termination sequences suggests that any transcription per se is not responsible for the inhibition of replication. Experiments shown in FIG. 4 demonstrated that the pBR region of pBC17(−) was transcribed, but that the transcription had little or no effect on plasmid replication. Also, in pHEN17 plasmids containing the CMV promotor, the UMS mitigated replication inhibition only when placed directly downstream of the promoter (FIG. 5). These results suggest that the inhibition of plasmid replication is due either to transcription through a specific region of the plasmid or transcription through a large region of the plasmid.

The data presented in FIG. 4C confirm that transcription has a direct role in the inhibition of plasmid replication. In the figure, the transcriptional activity and orientation of the CMV promoter/enhancer on these plasmids was qualitatively confirmed by slot blot analysis. The pBR probe shows a strong signal for pBC17(−) RNA, consistent with transcription directed by the CMV promoter in the negative direction. This plasmid was shown to replicate (FIG. 4B). This data suggests that transcription through this region does not inhibit replication, presumably due to the termination of transcription by the TK terminator (FIG. 4A).

The 17 probe (FIG. 4A) shows a strong signal for pBC17(+), consistent with transcription from the CMV promoter oriented in the positive direction, while no signal is detected for the UMS-containing plasmid pBUC17(+) by the 17 probe. This result is consistent with the termination of transcripts emanating from the CMV promoter by the UMS.

The above data suggest that transcription from promoter elements causes the inhibition of plasmid replication.

However, since transcription through the pBR region has little or no negative effect on the replication of pBC17(−), it appears that either transcription through a specific region or transcription through a large region of the plasmid may be responsible for the inhibition of plasmid replication. The transcribed pBR sequences are not responsible for plasmid replication activity in mammalian cells, as shown by the lack of replication of pHEN (FIGS. 1, 2 and 5).

In all of the above plasmid constructs demonstrating increased plasmid replication ability in the presence of UMS sequences, the introduced termination sequences block transcription from the CMV promoter through the sequences associated with nuclear retention (FIG. 4A, "Family") or with plasmid replication functions (FIGS. 1A and 4A, "Human 17").

These results demonstrate that to insure effective mammalian vector replication and maintenance, transcription units introduced into such vectors should be 3'-terminated or flanked by transcription termination sequences.

The results presented above demonstrate that promoter elements inhibit the replication of autonomous plasmids in human cells. Replication activity can be restored by placing a transcription termination sequence downstream of the promoter element. Previous studies have suggested that autonomous replication in mammalian cells does not initiate at fixed origin sequences (Krysan, et al., 1991, 1993; Heinzel, et al., 1991). Physical mapping studies demonstrated that replication on plasmids containing a human insert initiated at many sites throughout the plasmid (Krysan, et al., 1991).

Since there is no single region required for replication initiation on human autonomously replicating plasmids, it is unlikely that transcription through a specific region would interfere with replication initiation. Experiments performed in support of the present invention are consistent with a model in which transcription prevents replication from initiating within actively transcribed regions. The results presented above suggest that transcription inhibits DNA replication on these plasmids and that the degree of inhibition is dependent on transcription strength. Thus, plasmids carrying promoter elements can replicate as long as active transcription is confined to small regions of the plasmid and sufficient non-transcribed sequences are available for replication initiation.

II. AUTONOMOUS REPLICATION IN RODENT CELLS.

A. SHORT-TERM REPLICATION IN HAMSTER CELLS.

The replication behavior of various extrachromosomal plasmids (Example 9) in the baby hamster kidney (BHK) cell line was examined. All plasmids carried nuclear retention sequences from the Epstein-Barr virus genome (Krysan, et al., 1989). In addition, some of the plasmids carried large fragments of human DNA which have been shown to direct autonomous replication in human cells (Krysan et al., 1989; 1993; Heinzel et al., 1991).

Rodent cells are not permissive for EBV replication (Yates et al., 1985). A short-term assay for DNA replication was used to confirm this finding for the BHK cell line used in the experiments described below. Example 10 describes the results of short term replication assays for expression of a number of EBV based vectors in rodent cells.

The following plasmids were used to transfect rodent cells (FIG. 6):

(i) p220.2 is an EBV vector which carries the full viral origin of replication, oriP, as well as a gene coding for the EBNA-1 protein. p220.2 can efficiently replicate as an extrachromosomal plasmid in human cells (Yates et al., 1985; DuBridge et al., 1987).

(ii) pDY⁻ s a derivative of p220.2 in which the region of dyad symmetry from the viral ori has been removed (Reisman et al., 1985; Krysan et al, 1989). pDY⁻ is defective for replication in human cells, but contains the EBV nuclear retention sequences.

(iii) pLIB41 is a derivative of pDY⁻ which carries a 21-kb fragment of random human DNA (Krysan, et al., 1989). pLIB41 can efficiently replicate as an extrachromosomal plasmid in human cells.

These three plasmids were transfected into hamster BHK cells. One day after transfection, the cells were split to new dishes and grown for two more days. Low-$M_r$ DNA was then isolated from the cells using the Hirt extraction protocol. The restriction enzyme MboI was used to determine if the plasmids had replicated in the hamster cells. Since digestion of DNA by MboI is blocked by prokaryotic adenine methylation, plasmids which have not replicated in the hamster cells will be resistant to cleavage. Any plasmid which has replicated two or more times in the hamster cells will be sensitive to digestion by MboI.

Figure 7:
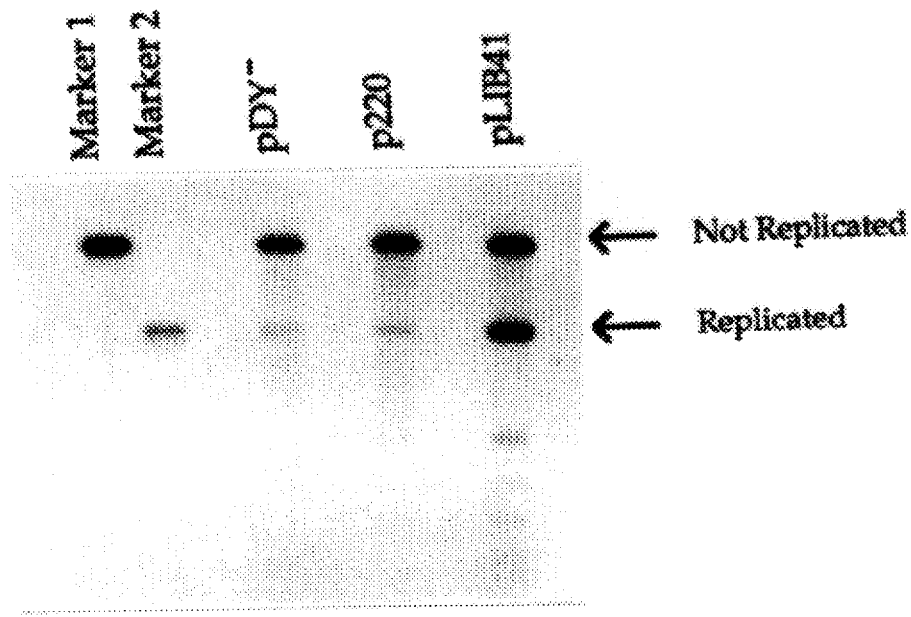
FIG. 7 shows data from short-term replication assays using hamster BHK cells transfected with the indicated plasmids.

The results presented in FIG. 7 demonstrate that pDY⁻ had replicated one or fewer times in the hamster cells. A similar result was obtained when the pDY⁻ vector was transfected into human cells—as expected since pDY⁻ has no functional origin of replication. The vector p220.2 also did not replicate in hamster cells. This result confirms that BHK cells are not permissive for EBV replication since the vector p220.2 contains the complete EBV origin of replication. On the other hand, about 50% of the plasmids recovered from the pLIB41 transfection replicated two or more times in the hamster cells.

Accordingly, the results demonstrate that hamster BHK cells do not support transient replication of EBV vectors. By contrast, the plasmid pLIB41, which carries a large fragment of human DNA, performed well in a transient replication assay in hamster cells.

Figure 8:
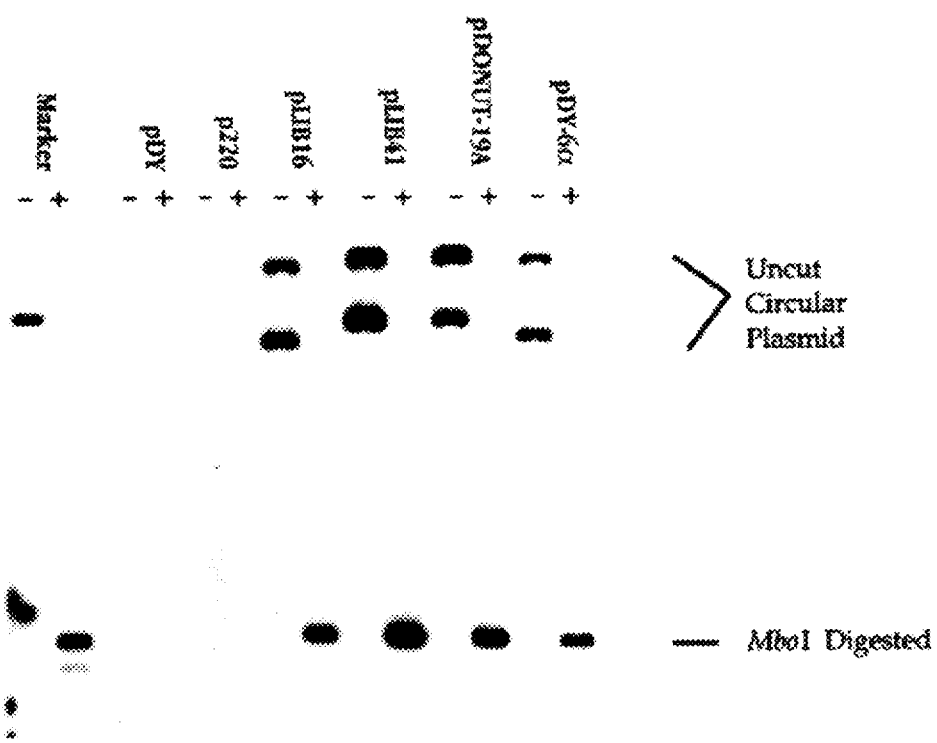
FIG. 8 shows data from long-term replication assays using hamster BHK cells transfected with the indicated plasmids and grown for seventeen days under hygromycin selection.

Further, using a long-term replication assay, experiments performed in support of the present invention demonstrated that neither pDY⁻ nor the wild-type EBV vector p220.2 were maintained at a detectable copy number following 17 days in hamster cells (Example 11, FIG. 8). However, four plasmids (including, pLIB41) carrying large fragments of human DNA were easily detectable after 17 days in hamster cells. Analysis using genomic DNA hybridization analysis revealed that the plasmids were being replicated as extrachromosomal molecules (Example 11).

These results demonstrate that the EBV nuclear retention function acts to stably maintain autonomously replicating, extrachromosomal plasmids in hamster cells and that large mammalian DNA fragments provide efficient replication in rodent cells.

B. ANALYZING THE REPLICATION OF PLIB41 USING A DENSITY SHIFT ASSAY.

A density shift assay was utilized to measure the number of times per cell cycle that pLIB41 replicated in BHK cells (Example 12). The plasmid pLIB41 replicates in a controlled, once per cell cycle manner in human cells (Haase, et al., 1991). EBV vectors replicate once per cell cycle in human cells as well (Haase, et al., 1991; Yates, et al., 1991).

The vector pLIB41 was transfected into Baby Hamster Kidney (BHK) cells and propagated in the presence and absence of 5-bromo-2'-deoxyuridine (BrdU). All of the recovered plasmid from BHK cells not labeled with BrdU banded in a single peak in the density gradient (FIG. 9A, LL).

One cell cycle in BHK cells is approximately 12 hours. For the cells grown in the presence of BrdU for 12 h the majority of the recovered plasmid banded at an intermediate density (FIG. 9A, HL), corresponding to plasmids replicated once during the labeling period. Some un-replicated plasmid was also detectable for the 12-h labeling (FIG. 9A, LL). No plasmid was detected having both strands containing BrdU (HH position). These results indicate that pLIB41 is replicating in a controlled, once per cell cycle manner.

Two complete cell cycles in BHK cells occur in 24 hours. Plasmid recovered after 24 hours of growth was equally distributed between the HL and HH peaks of the density gradient (FIG. 9A). This result demonstrates that labeling during the two cell cycles most of the plasmids replicated two times and are replicating with high efficiency.

Figure 9A:
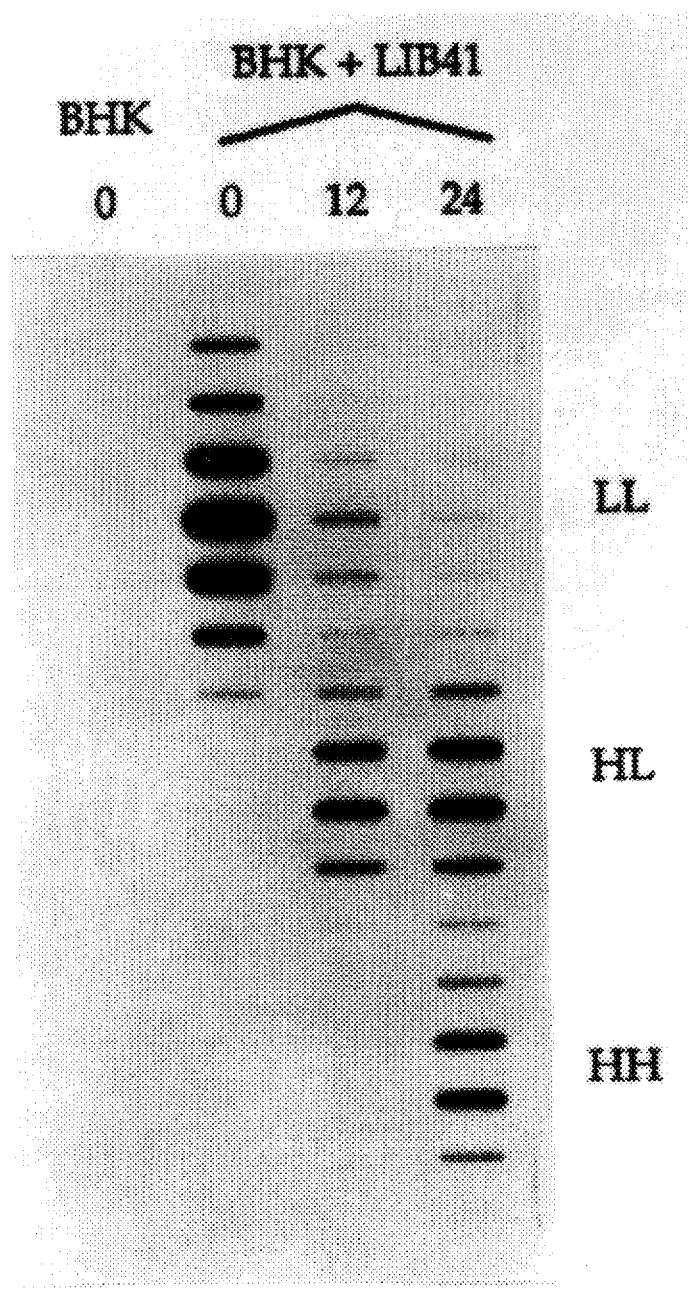
FIGS. 9A and 9B show data from density labeling replication experiments.
Figure 9B:
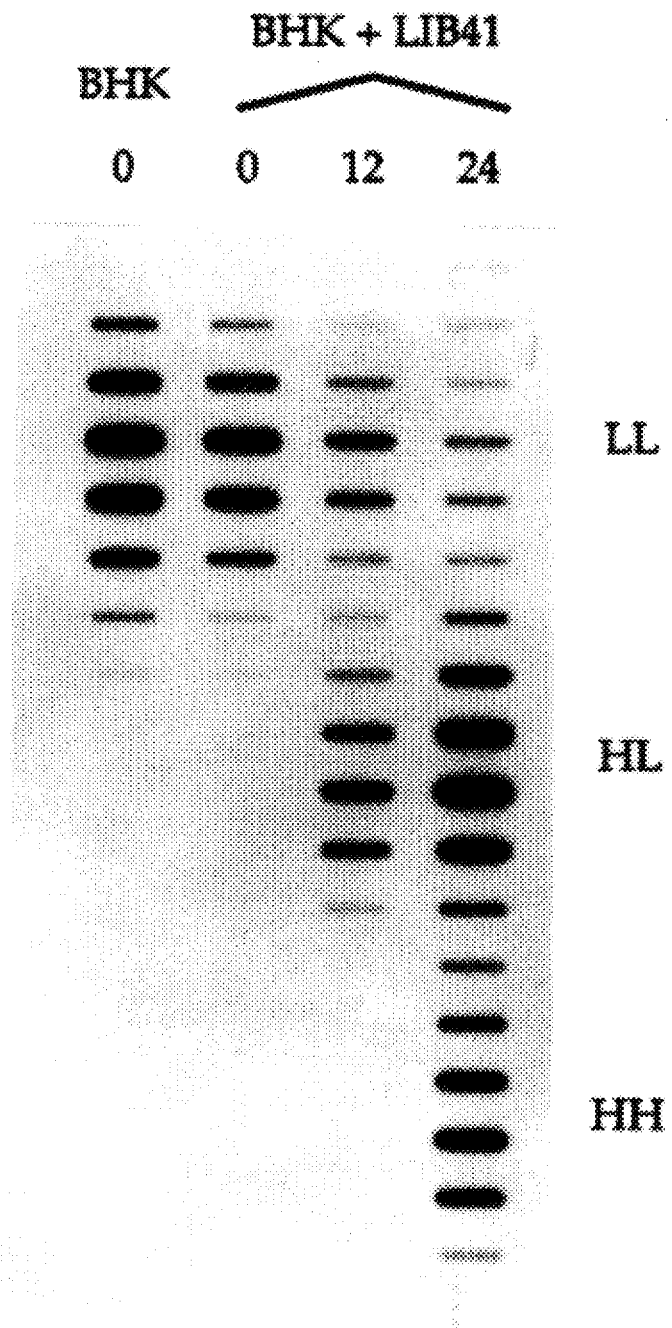

Further, the autoradiogram presented in FIG. 9B depicts the result of using a hamster chromosomal DNA probe to hybridize with DNA bound to the slot blot seen in FIG. 9A (Example 12). The patterns of replication seen using the chromosomal probe were similar to those seen using the plasmid probe. This result demonstrates that plasmid DNA replicated in a manner similar to chromosomal sequences.

These results from density labeling experiments using 5-bromo-2'-deoxyuridine (BrdU) demonstrate that the plasmid pLIB41 replicates in a controlled, once per cell cycle manner in hamster cells. In addition, the density labeling experiment showed that pLIB41 replicates with a high per generation efficiency, similar to that of the hamster chromosomes.

C. EVIDENCE THAT EBNA-1 IS EXPRESSED IN HAMSTER CELLS.

The results presented above have demonstrated that the EBV vector p220.2 is defective for replication in hamster BHK cells. The conclusion that BHK cells are not permissive for EBV replication assumes that EBNA-1 is adequately expressed from p220.2 in hamster cells. To validate this assumption, it was experimentally determined if a biologically relevant level of EBNA-1 was being expressed in BHK cells transfected with p220.2. The follow experiments also demonstrate that expression of EBNA-1 is required for the nuclear retention of autonomously replicating plasmids such as pLIB16.

Example 13 describes the results obtained from transient drug resistance assays carried out in BHK cells. The transient drug resistance assay is based on a phenomenon (Reisman et al., 1985) in which human cells transfected with pDY⁻ (which carries the hygromycin resistance gene) give rise to thousands of drug-resistant colonies after two weeks of hygromycin selection. Although pDY⁻ is defective for replication, the EBV nuclear retention function is able to retain enough transfected DNA in the human cells to allow for survival during the first two weeks of drug selection.

However, if the cells are propagated for an additional two weeks under Hyg selection, most of the cells transfected with pDY⁻ die, leaving only a few colonies due to plasmids integrating into the human chromosomes. This transient drug resistance phenotype is dependent on both the EBV family of repeats and EBNA-1 (Reisman et al., 1985).

Transient drug resistance is therefore useful as a biological assay for the production of significant levels of EBNA-1 in transfected cells. The following plasmids were transfected into hamster BHK cells: pBODY, pDY⁻, p220.2, pBODY-16, pLIB16 (Example 13). The vectors pBODY and pBODY-16 do not carry EBNA genes.

The results of this analysis demonstrated that only the cells transfected with pDY⁻, p220.2, and pLIB16 resulted in a large number of drug resistant cells after the first five days of Hyg selection. No drug resistant colonies were detected for cells transfected with pBODY or pBODY-16. These results suggest that the EBNA-1 gene is being expressed in hamster cells.

Cells transfected with pDY⁻, p220.2, and pLIB16 were then grown for an additional five days under Hyg selection. Cells transfected with p220.2 and pDY⁻ were sparse at day ten. This result is consistent with defective replication of these plasmids in hamster cells. Cells transfected with pLIB16 completely covered the plate at the ten day time point. This result is consistent with the plasmid being efficiently replicated and maintained as an extrachromosomal molecule.

The above data demonstrate that the vectors p220.2 and pDY⁻ gave rise to the characteristic transient drug resistance phenotype in hamster cells, indicating that EBNA-1 was expressed. The data further support the conclusion that hamster cells are not permissive for EBV replication. EBNA-1 and the family of repeats appear to supply the same nuclear retention function in hamster cells that they do in human cells. However, since hamster cells are not permissive for EBV replication, this result suggests that nuclear retention and replication are functionally separate.

In contrast, four different human fragments produced vectors that replicated efficiently in rodent cells. Most large fragments of eukaryotic DNA can be used in combination with the EBV components to generate vectors that replicate efficiently in rodent cells.

Autonomously replicating plasmids can be developed for other eukaryotic species for which such vectors are not currently available. The family of repeats and EBNA-1 are used to supply the plasmids with a nuclear retention function, while appropriate genomic sequences (e.g., large sections of genomic DNA) supply the ability to replicate in a selected host cell.

III. ANIMAL DISEASE MODELS.

The vectors of the present invention are useful for in vitro studies of gene expression in animal models, in particular, the studies of the expression of genes that provide therapeutic effects. The vectors of the present invention are particularly well suited to this purpose in view of the ability of the vectors to replicate in mammalian and rodent cells. Accordingly, in vitro effects of a selected vector can be confirmed in an in vivo system.

A number of disease models have been established in animals, including, but not limited to, the following (target—model system): hepatitis virus—chimpanzee or monkey models; c-myb, c-myc, bcr-abl—SCID mouse models (e.g., Ratajczak, et al.); NF-κB—mouse (Higgins, et al.); p120—mouse (Perlakey, et al.); and cystic fibrosis (Higgins, et al., 1992; Coutelle, et al., 1993; Hyde, et al., 1993).

The vectors of the present invention provide the ability to efficiently transfect large numbers and diverse populations of somatic cells in adult animals to analyze the function of genes transferred and expressed in vivo. An exemplary animal model for evaluation of gene expression is expression in rodents and rodent cells (Example 16). Zhu, et al., (1993) have described the use of intravenous injection of various mixtures of expression plasmids and [1-(2,3-dioleyloxy)propyl]-N,N,N-trimethylammonium chloride (DOTMA):dioleoyl phosphatidylethanolamine (DOPE) to deliver nucleic acids to a wide variety of mouse tissues.

Vectors of the present invention, carrying for example a reporter gene, can be injected into mice and the resulting tissue specific expression assayed (Example 16). Further, the vectors of the present invention can be used to deliver genes of interest, such as the cystic fibrosis transmembrane conductance regulator (CFTR) gene, into an animal subject. For example, transgenic mice with disrupted cftr genes (homozygous) as a cystic fibrosis model for the evaluation of gene therapy protocols (Hyde, et al., 1993). As described above, liposomes are used to deliver a CFTR expression plasmid to epithelia of the animal's airway and to alveoli deep in the lung. The effect of introduction of the plasmid is typically evaluated by evaluation of ion conductance in the trachea of transgenic homozygous cftr-defective mice. Studies such as these provide means to examine the feasibility of gene therapy for the pulmonary aspects of cystic fibrosis in humans (Hyde, et al., 1993).

These in vivo experiments can be used to verify that foreign genes can be expressed from the vectors of the present invention over a long time course. Obtaining long-term expression has been a problem for retrovirus vectors, where gene expression often turns off (Mulligan, 1993), and for adenovirus vectors and conventional plasmid vectors, where the presence of vector DNA in the cells is short-lived. Long-term expression of the hygromycin resistance gene has been observed using the vectors of the present invention.

Further long-term studies, in animal models or cell cultures, may be carried out as follows. A reporter gene (such as, β-galactosidase, CAT or luciferase) is (i) placed under the transcriptional under control of a promoter that is functional in the target cell (e.g., the CMV promoter), and (ii) flanked by transcription termination sequences (e.g., the mouse UMS sequence). This expression cassette is cloned into a vector of the present invention.

Expression of the reporter gene is assayed. For example, expression of the β-galactosidase gene is easily monitored by staining the cells with X-gal. The assay can also be done quantitatively on a per cell basis using the FACS (Fiering, et al., 1991; Nolan, et al., 1988).

To confirm these results, we will also use a construct containing the chloramphenicol acetyl transferase (CAT) gene (e.g., Example 14). The β-galactosidase and CAT assays are carried out on cells transfected with the plasmids over the course of at least two months.

An exemplary cell line for initial studies is the 293 cell line, a human embryonic kidney cell line. Expression of the gene is then evaluated in in vivo mouse experiments. Expression of genes carried in the vectors of the present invention can be assayed in additional cell types, including, lymphocytes (Heinzel, et al., 1991; Gussoni, et al., 1992; Cristiano, et al., 1993).

The method of introduction of vectors into cells is typically lipofection. It has been shown that this method is effective and non-toxic in vivo (Alton, et al., 1993; Hyde, et al., 1993; Philip, et al., 1993; Stribling, et al., 1992; Zhu, et al., 1993), and it is applicable to a broad range of cell types.

Exemplary genes for testing in cell culture and animal models include the following: cystic fibrosis transmembrane conductance regulator, the factor IX gene, and the dystrophin gene (Alton, et al., 1993; Cristiano, et al., 1993; Gussoni, et al., 1992; Zhu, et al., 1993).

Studies in other rodent and animal models (e.g., Pursell, et al., 1989) allow similar evaluation of a given vector construct for gene therapy potential in human subjects.

IV. UTILITY.

A. THE VECTORS OF THE PRESENT INVENTION.

The two components of the vectors of the present invention that are required for nuclear retention comprise the EBNA-1 gene, which encodes EBV Nuclear Antigen-1 protein, and the family of repeats, a portion of the EBV latent ori. Nuclear retention appears to be mediated by specific binding of EBNA-1 to the family of repeats (Rawlins et al., 1985) and non-specific binding of the EBNA-1—plasmid complex to the chromosomes (Harris et al., 1985; Krysan et al., 1989).

For stable replication and maintenance, the vectors of the present invention have the following components:

(i) the Epstein Barr Virus (EBV) family of repeats and a functional copy of the EBNA-1 gene (Sugden, 1987, herein incorporated by reference; Baer, et al., 1984; Yates, et al., 1985), i.e., the gene is under the transcriptional control of a promoter that is transcribed in host cells. The region of dyad symmetry in the EBV oriP region is not required.

(ii) mammalian DNA fragments typically larger than approximately 10 kb that are capable of supporting efficient autonomous replication in the mammalian host cells, for example, human DNA in human cells (Krysan, et al., 1989; Heinzel et al., 1991) and human DNA in rodent cells (see above). Large fragments of DNA heterologous to the host cell, preferably eucaryotic genomic DNA, can also support autonomous replication of the present vectors in host cells, for example, large fragments of yeast DNA support replication in human cells (Tran, et al., 1993). These results suggested that the initiation of DNA replication in human cells may have little need for specific sequences to serve as origins of replication. In one embodiment, exemplary large genomic DNA fragments, for use in the vectors of the present invention, are randomly generated human genomic DNA fragments, typically in the size range of approximately 8 kb to approximately 20 kb. Other sizes of large genomic DNA fragments can be used in vector constructs and the replication and stability of the resulting vector evaluated as described herein.

In addition the vectors of the present invention typically carry an expression cassette containing a gene of interest (such as a reporter or therapeutic gene) under the transcriptional control of a suitable promoter (i.e., one that allows expression in the selected host cell) where transcription from the promoter is substantially terminated to reduce or eliminate transcription into the large segment of mammalian DNA described above. Transcription through any selected transcription termination sequence into adjacent 3' sequences can be evaluated as described in Example 7 (FIG. 4C).

Such expression cassettes may have single or multiple transcription termination signals at the coding-3'-end of the gene being expressed (for example, UMS, described above, and SV40 or Herpes Simplex Virus I (HSV-I) transcription termination sequences). Also, both ends of the expression cassette may be flanked by transcription termination sequences. Alternatively, the EBV family of repeats and the large fragment of genomic DNA can be flanked by transcription termination sequences.

Further, the vectors of the present invention may include selectable markers for use in mammalian cells (such as, the hygromycin resistance gene or neomycin resistance gene). The vectors may also include sequences that allow their selection and propagation in bacterial or yeast host cells. Such sequences are well known in the art and are commercially available as well (e.g., Clontech, Palo Alto, Calif.; Stratagene, La Jolla, Calif.).

The extrachromosomal vectors of the present invention, that replicate stably under correct once-per-cell cycle control and are retained in cells over the long-term, are useful tools for studying gene expression, DNA replication, repair, recombination, and other cellular processes, and have potential importance for gene therapy. Such vectors have been heretofore unavailable for rodent cells, even though these cells are commonly used in understanding the biology of mammalian systems. Further, vectors that replicate in both rodent and primate (e.g., human) cell types have been similarly unavailable.

The vectors of the present invention are useful for the expression of nucleic acid coding sequences in mammalian cells. For example, a selected peptide or polypeptide coding sequence can be inserted in an expression cassette of a vector of the present invention. The vector transformed into host cells, the host cells cultured under conditions to allow the expression of the protein coding sequences, and the expressed peptide or polypeptide isolated from the cells.

B. APPLICATIONS IN RODENT CELLS.

As described above, stable, autonomously replicating vectors (that replicate once per cell cycle) for rodent cells have not been previously described. In rodent cells Bovine Papilloma Virus (BPV) and polyoma vectors are autonomously replicating, but they rearrange and do not replicate once per cell cycle (Gilbert, et al., 1987; DuBridge, et al., 1988; Lebkowski, et al., 1984). The experiments performed in support of the present invention demonstrate the ability of the vectors of the present invention to be retained in the nucleus of rodent cells and to be stably replicated therein.

The ability to transfer genes between rodent and human cells has important implications, particular in the realm of gene therapy, where potential gene therapies are explored in rodent models as feasibility studies for use of such therapies in human subjects. In recent years numerous rodent models for human disease have been developed (see above). Accordingly, an important advantage of the methods and vectors of the present invention is the ability of the vectors to replicate and be stably retained in both rodent and human cells. For example, testing of vectors of the present invention carrying the CFTR gene for the treatment of cystic fibrosis can be undertaken, first in a rodent model, then in human studies.

In addition to these gene therapy related uses of the vectors of the present invention, the ability of the vectors to transfect rodent cells can also useful for drug screening in rodent cells (in vitro or in vivo). For example, a promoter region from a selected gene of interest (such as a cytokine, interleukin or interferon gene) can be fused to a reporter gene (such as CAT). This gene fusion can be incorporated in an expression cassette in a vector of the present invention. The vector is then transfected into rodent cells. The transfected rodent cell can then be used to screen for compounds effective to affect the level of transcription of the reporter gene. For example, drugs can be identified that up regulate expression of a selected interferon gene (Johnson, et al., 1994).

Candidate compounds for screening assays can be obtained from a number of sources, including but not limited to, the following. Many pharmaceutical companies have extensive libraries of chemical and/or biological mixtures, often fungal, bacterial, or algal extracts, that would be desirable to screen with the assay of the present invention. Such compounds, or molecules, may be either biological or synthetic organic compounds, or even inorganic compounds (i.e., cisplatin).

Further, the vectors of the present invention can be used to generate transgenic mice useful in methods for determining the oncogenic potential of chemical compounds (Berns, 1989; herein incorporated by reference). In this method, a transgenic mouse predisposed to T-cell lymphomas is employed; such a transgenic mouse can carry, for example, copies of the pim-1 oncogene in a vector of the present invention.

C. GENE THERAPY APPLICATIONS.

The vectors of the present invention are useful in human and veterinary gene therapy applications. The vectors can be introduced into a treatment subject by a number of methods known in the art, for example, liposome formulations introduced parenterally (Zhu, et al., 1993) or by aerosol (Stribling, et al., 1992).

The vectors of the present invention can be used for direct gene replacement therapy, as in the case of replacing the function of a non-functional gene (e.g., cystic fibrosis or sickle cell anemia (Hyde, et al., 1993). Such direct replacement therapies have useful veterinary applications as well (Smith, 1994; Kay, et al., 1994).

In addition the vectors can be used to produce anti-sense nucleic acids in target cells. Antisense therapy involves the production of nucleic acids that bind to a target nucleic acid, typically an RNA molecule, located within cells. The term antisense is so given because the oligonucleotides are typically complementary to mRNA molecules ("sense strands") which encode a cellular product (Matsukura, et al., 1989; Agrawal, et al., 1989; Zamecnik, et al., 1986; Rittner, et al., 1991; Stein, et al., 1993). Vectors can be designed to express "anti-sense" nucleic acid molecules (Behrend, et al., 1994; Lewalle, et al., 1993; Zhang, et al., 1993; Fujita, et al., 1993) targeted to selected cellular (e.g., oncogene) or viral gene expression products.

Exemplary modes by which sequences can be targeted for therapeutic applications include: blocking the interaction of a protein with an RNA sequence (e.g., the interaction of RNA virus regulatory proteins with their RNA genomes); and targeting sequences causing inappropriate expression of cellular genes or cell proliferation (e.g., genes associated with cell cycle regulation; genetic disorders; and cancers (protooncogenes)).

Exemplary potential target sequences are protooncogenes, oncogenes/tumor suppressor genes, transcription factors, and viral genes.

In addition, the vectors of the present invention can be used to deliver DNA sequences encoding catalytic RNA molecules (Castanotto, et al., 1992; Lo, et al., 1992) into cells. For example, DNA sequences encoding a ribozyme of interest can be cloned into a vector of the present invention. Such a ribozyme may be a hammerhead ribozyme (Taylor, et al., 1992) capable of cleaving a viral substrate, such as the Human Immunodeficiency Virus genome (Dropulic, et al., 1993), or an undesirable messenger RNA, such as that of an oncogene. The DNA-encoding ribozyme sequences can be expressed in tandem with tRNA sequences, with transcription directed from, for example, mammalian tRNA promoters.

The present invention includes pharmaceutical compositions useful in gene therapies. The compositions comprise an effective amount of a vector of the present invention in combination with a pharmaceutically acceptable carrier. One or more vector, containing different gene coding sequences of interest, may be included in any given formulation.

Typically, the vectors are administered associated with (Zhu, et al., 1993) or in lipid/liposome carriers. The use of liposomes to facilitate cellular uptake is described, for example, in U.S. Pat. Nos. 4,897,355 (Eppstein, D., et al., issued 30 Jan. 1990) and 4,394,448 (Szoka, F., et al., issued 19 Jul. 1983). Numerous publications describe the formulation and preparation of liposomes.

For parenteral administration, sterile liquid pharmaceutical compositions, solutions or suspensions can be utilized by, for example, intraperitoneal injection, subcutaneous injection, intravenously, or topically. The vectors can be also be administered intravascularly or via a vascular stent.

In addition, the vectors can be formulated for inhalation. The liquid carrier for pressurized compositions can be halogenated hydrocarbon or other pharmaceutically acceptable propellent. Such pressurized compositions are typically lipid encapsulated or associated for delivery via inhalation. For administration by intranasal or intrabronchial inhalation or insufflation, the vectors may be formulated into an aqueous or partially aqueous solution, which can then be utilized in the form of an aerosol, for example, for treatment of conditions affecting the respiratory tract, such as cystic fibrosis.

The dosage requirements for treatment with the vectors of the present invention vary with the particular compositions employed, the route of administration, the severity of the symptoms presented, and the particular subject being treated. In general, concentrations of the vector are administered that provide effective results without causing any harmful or deleterious side effects (e.g., an effective amount).

As discussed above for rodent cells, the vectors of the present invention can be used in drug screening methods involving human cells or other mammalian cells.

The following examples illustrate, but in no way are intended to limit the present invention.

MATERIALS AND METHODS

E. coli DNA polymerase I (Klenow fragment) was obtained from New England Biolabs (Beverly, Mass.). T4 DNA ligase and T4 DNA polymerase were obtained from Boehringer Mannheim Biochemicals (Indianapolis, Ind.). General molecular biology reagents, including restriction endonucleases, are obtained from a number of commercial sources and typically used following the manufacturer's instructions.

Synthetic oligonucleotide linkers were purchased, for example, from New England Biolabs (Beverly, Mass.). Random primers were obtained from Pharmacia Biotechnology (Piscataway, N.J.).

Standard manipulations of molecular biology have been carried out as previously described (Ausubel, et al.; Sambrook, et al.; Maniatis, et al.).

Cell Lines. The cell line 293S is a human embryonic kidney fibroblast cell line (Stillman, et al., 1985). The cell line 293S/EBNA is a derivative of 293S, into which an EBNA-1 expression unit has been integrated (Heinzel, et al., 1991). 293S and 293S/EBNA cells were grown at 37° C. in a 5% $CO_2$ incubator, in Dulbecco modified Eagle medium containing 10% fetal calf serum, penicillin, and streptomycin.

EXAMPLE 1

PLASMID CONSTRUCTION

The plasmid pMLλ (Heinzel, et al., 1991) was created by cloning a 2.2 kb Sau3A fragment from the bacteriophage λ genome into pML, a 2.9 kb derivative of pBR322 which was isolated from the plasmid pJYM (Lusky, et al., 1981).

The plasmid pHEN was created by the digestion of pMLλ with HindIII and EcoRV, followed by the cloning of a 156 bp HindIII-EcoRV fragment from the plasmid pNUT (Heinzel, et al., 1991) into the HindIII-EcoRV sites of pMLλ. The HindIII-EcoRV fragment from pNUT is identical to the one present in pMLλ, except that it contains a NotI site. This fragment encompasses pBR322 sequences 29–189 (Sambrook, et al.).

The plasmid pDonut17B (the vector pDONUT, see Example 11, with a 16.5 kb insert of randomly generated human genomic DNA) was digested with NotI to release the 16.5 kb fragment of human DNA (herein designated the human 17 fragment) (Heinzel, et al., 1991). The human 16.5 kb fragment was cloned into pHEN to create pHEN17. FIG. 1A shows a map of the plasmid pHEN17. The sites of promoter placement and orientation are indicated. The thick black line indicates the human 17 fragment. The map is drawn approximately to scale. In the figure: E, EcoRI; H, HindIII; N, NotI; M, MboI.

The plasmid pH17 is pNUT with the human fragment 17 cloned into the HindIII site. The plasmids pH172 and pH174 were constructed by cloning the 2 kb and 4 kb NotI human fragments from pPG2B and pPG4A (Heinzel, et al., 1991) into the NotI site of pH17.

A fragment was isolated containing the promoter and enhancer elements from the major immediate early gene of the human cytomegalovirus (CMV) (Boshart, et al., 1985). This fragment contains the CMV IE1 sequences −677 to +79 (Boshart, et al., 1985; Thomsen, et al., 1984). The CMV IE1 region −677 to +79 was isolated from the pRCMV expression vector (I. Caras, Genentech).

The plasmid pRCMV was digested with ScaI and XbaI and the fragment containing CMV sequences was cloned into pUC19 (Gibco-BRL, Gaithersburg, MD), which had been digested with SmaI and XbaI. The resulting plasmid was digested with HindIII to release a 778 bp CMV fragment, which contains 24 bp from the pUC19 polylinker (from the XbaI to HindIII sites). The 0.8 kb CMV HindIII fragment was cloned into the unique HindIII site of pHEN in both orientations, and the 16.5 kb human NotI DNA fragment was added to the NotI site to create the plasmids pHC17(−) and pHC17(+).

A 4.3 kb β-actin promoter fragment (Ng, et al., 1985) from the plasmid phβAPr-3P-NEO (L. Kedes, University of Southern California, Los Angeles, Calif.; Ng, et al., 1985) was cloned into the plasmid pUCH, a derivative of pUCR, (Heinzel, et al., 1988) on EcoRI ends to create the plasmid pUCHBA. The SalI site was destroyed in the polylinker by digesting pUCHBA with SalI and filling in the overhang with Klenow polymerase. The β-actin fragment was then excised with EcoRI and cloned into pHEN in both orientations to create pHBA(+) and pHBA(−). Blunt ends were created on the human 16.5 kb NotI fragment by treatment with T4 DNA polymerase. It was then ligated into the plasmid pUCR, which had been digested with SmaI.

The human 16.5 kb fragment was then removed from pUCR as a SalI fragment and cloned into pHBA(+) and pHBA(−) to create pHB17(+) and pHB17(−).

The 460 bp XhoI/EcoRI fragment containing the tetracycline-responsive promoter (Gossen, et al., 1992) was removed from the plasmid pUHD10-3 (M. Gossen and H. Bujard, Universität Heidelberg, Germany; Gossen, et al., 1992) and cloned into the SalI/EcoRI site of pUCR. The promoter fragment was removed on HindIII ends and cloned into pHEN in both orientations. The 16.5 kb human fragment was then added to create pHT17(+) and pHT17(−). The plasmid pUHD15-1 (Gossen, et al., 1992) contains the tTA gene driven by the hCMV promoter (Gossen, et al., 1992).

The plasmid pBODY was generated by partial digestion of pHEBo (Yates, et al., 1985) with EcoRV, followed by complete digestion with HpaI and re-circularization by ligation of the digestion products. pBODY was the resulting ligation product missing only the 140 bp EBV dyad-containing region (Krysan, et al., 1989). pBODY17 was created by cloning the 16.5 kb human fragment 17 into the SalI site of pBODY. The plasmids pBC17(+) and pBC17(−)

were created by first cloning the 0.8 kb CMV fragment in both orientations into the HindIII site of pBODY and then cloning the 16.5 kb human fragment 17 into the SalI site.

A 1027 bp SacI-XbaI fragment containing a putative transcriptional terminator, termed upstream mouse sequence (UMS), was isolated from the plasmid pHTMS23 (McGeady, et al., 1986). This fragment was blunt-ended with T4 DNA polymerase and ligated into the plasmid pUCR, which had been digested with SmaI. In order to create pBUC17(+) and pBUC17(−), the UMS fragment was excised from pUCR on BamHI ends and cloned into the BamHI site of pBODY plasmids containing the CMV promoter in both orientations. The 16.5 kb human fragment 17 was then cloned into the SalI site.

The plasmids pHENU and pHEN17U were created by excising the UMS fragment on EcoRI sites from the pUCR plasmid and cloning it into the EcoRI sites of pHEN and pHEN17 respectively. The UMS fragment was cloned into the EcoRI sites of pHEN plasmids containing the CMV promoter in both orientations and then the human fragment 17 was cloned into the NotI site in order to create pHUC17 (+) and pHUC17(−).

A summary of plasmid constructions is presented in FIG. 10.

EXAMPLE 2

REPLICATION ASSAYS

A. STANDARD ASSAYS 293S cells (Bruce Stillman, Cold Spring Harbor Laboratory, Cold Spring Harbor, N.Y.; Stillman, et al., 1985) were grown to 80–90% confluency on 100-mm dishes. The cells were split 1:20 into 60-mm dishes containing 5 ml of fresh medium (Dulbecco modified Eagle medium (DMEM); Gibco BRL, Grand Island, N.Y.) and grown for twenty-four hours. Cells were transfected with equimolar amounts of plasmid DNA using calcium phosphate co-precipitation (Wigler, et al., 1979).

One day following transfection, the growth medium was replaced with fresh medium. Two days post-transfection, plates were split 1:4 into 60-mm dishes. Four to five days post-transfection, plasmid DNA was recovered by the method of Hirt (1967).

For the pBODY plasmids, plasmids were transfected into 293S/EBNA cells essentially as described by Heinzel, et al. (1991).

One-fourth of the sample extracted from a single 60-mm dish was digested with HindIII and MboI, (EcoRI and MboI for pBODY plasmids) electrophoresed on a 0.65% agarose gel, transferred to "ZETAPROBE" membrane (Bio-Rad, Richmond, Calif.) using 0.4N NaOH as the transfer buffer. DNA bound to the membrane was probed with $^{32}$P-labeled DNA fragments labelled with random primers (Pharmacia, Piscataway, N.J.).

Autoradiograms were scanned with a Molecular Dynamics 300A computing densitometer, using volume integration for quantification of all bands.

B. REPLICATION ASSAYS USING THE TETRACYCLINE-RESPONSIVE PROMOTER

Equimolar amounts of plasmid DNA (approximately 5 µg) were co-transfected with 200 ng of the tTA expression vector, pUHD15-1 (Gossen, et al., 1992). In experiments where tetracycline was used, the appropriate concentration of tetracycline was added to the cells when the media was changed one day after the transfection. The appropriate concentration of tetracycline was maintained after splitting the cells 2 days post-transfection. Cells were harvested five days post-transfection.

EXAMPLE 3

STEADY STATE RNA ASSAY

The appropriate plasmids were transfected into 293S/EBNA cells by calcium phosphate co-precipitation. After 4 days in culture, total cellular RNA from a 75% confluent 100-mm dish was isolated using a guanidium thiocyanate/cesium chloride procedure (MacDonald, et al., 1987). RNA pellets were resuspended in 90 µl of water and 10 µl of medium salt restriction enzyme buffer (Buffer "M", Boehringer Mannheim Biochemicals, Indianapolis, Ind.). Samples were treated with 1 µl of RNAse-free DNAse for 1 hour at 37° C. The reaction was stopped by adding 20 µl of 100 mM EDTA/2% SDS and 80µl of water. Samples were extracted with phenol/chloroform and precipitated with 0.1 volume of sodium acetate and 2.5 volumes of ethanol at −20° C. RNA pellets were resuspended in 75 µl of water.

Samples were quantitated on a Bausch and Lomb "SPECTRONIC 1001" spectrophotometer. Twenty micrograms of each RNA sample were denatured in 100 µl of 0.1M NaOH and slot-blotted onto a "ZETAPROBE" membrane (Bio-Rad, Richmond, Calif.). Hybridization was performed as described above.

EXAMPLE 4

INHIBITION OF PLASMID REPLICATION BY PROMOTER ELEMENTS

Cells were transfected (Example 2) with the vectors (Example 1) shown in FIGS. 1B, 1C and 1D. Hirt extracts taken four days post-transfection (Example 2) were digested with MboI and HindIII and run on agarose gels. The DNA was transferred to membranes and DNA hybridization analysis carried out on the MboI/HindIII digested Hirt extracts (Example 2). The membranes were probed with a 2.2 kb (MboI/DpnI) lambda fragment present in the vector backbone. The membranes were exposed to X-ray film. A photograph of a resulting autoradiogram is shown in FIG. 1B.

In FIG. 1B: the 7.3 kb band represents DNA that has replicated one or zero times in human cells; the 2.2 kb band represents DNA that has replicated two or more times in human cells; M1 and M2 are size markers created by digesting 0.5 ng pHEN with HindIII (M1) and 0.5 ng of pHEN with DpnI (M2).

The restriction enzyme MboI is methylation sensitive and will only cleave DNA molecules that have replicated two or more times in human cells; replication in human cells results in loss of their bacterial methylation pattern. The 7.4 kb band represents DNA that was not digested by MboI and thus has replicated once or not at all, while the 2.2 kb MboI band represents DNA that has replicated at leasttwice.

Plasmid replication was readily detectable for the positive control, pHEN17, while little or no replication was detectable for the negative control, pHEN. The replication activities of the plasmids containing either the CMV or β-actin promoter elements in either orientation were markedly reduced when compared to pHEN17. The plasmids pHC17 (+) and pHC17(−) showed an approximately 5-fold reduction, and the plasmids pHB17(+) and pHB17(−) showed an approximately 10-fold reduction in MboI sensitive DNA.

Two randomly isolated human genomic fragments, sized 2 kb and 4 kb, were cloned into the HindIII site of pH17 to control for the effects of inserting DNA fragments into the plasmid. The plasmid pH17 that differs from pHEN17 by a single restriction site. The replication activities of these two plasmids, pH172 and pH174 were similar to the activity of pHEN17 suggesting that the addition of DNA sequences to this site does not have a negative effect on the replication of the plasmid.

In order to confirm that the plasmids were being maintained extrachromosomally, Hirt extracts were run undigested on an agarose gel. The gel was blotted and probed with the 2.2 kb (MboI/DpnI) lambda fragment. The results are shown in FIG. 1C. In the figure, the positions of super-coiled, S.C., and nicked circle, N.C., are indicated. All of the plasmids ran as super-coiled and nicked circles, indicating that they were predominantly extrachromosomal.

In order to confirm that the replication activity observed in FIG. 1B was occurring on autonomous plasmids, Hirt extracts were digested with DpnI. The restriction enzyme DpnI is methylation sensitive and will only digest DNA that contains a bacterial methylation pattern. Thus, DNA that has replicated 1 or more times in human cells is not sensitive to digestion. The DpnI digested extracts were run on agarose gels, blotted and probed with the 2.2 kb (MboI/DpnI) lambda fragment. The results are shown in FIG. 1D. In the figure, the positions of super-coiled, S.C., and nicked circle, N.C., are indicated. The four bp DpnI recognition sequence occurs frequently; small DpnI-digested fragments ran off the bottom of the gel and are not shown.

In FIG. 1D, plasmid DNA that replicated in human cells and was not digested by DpnI ran as super-coiled and nicked circles. In confirmation of the results shown in FIG. 1B, replicated DNA was readily detectable for pHEN17, pH172 and pH174, while the replication activity of the negative control, pHEN, and the plasmids containing promoter elements, pHC17(+), pHC17(−), pHB17(+) and pHB17(−), was markedly reduced. Furthermore, this data confirmed that these plasmids were replicating as autonomous plasmids.

EXAMPLE 5

CONDITIONAL INHIBITION OF PLASMID REPLICATION BY THE TETRACYCLINE-RESPONSIVE PROMOTER

The two plasmids, pHT17(+) and pHT17(−), were generated by placing the tetracycline-responsive promoter into the HindIII site of pHEN17 (Example 1). The plasmids (see FIG. 2) were transfected into 293S cells, and assayed for replication activity in the MboI assay described above (Example 2).

Hirt extracts were harvested five days post-transfection from transfected cells. The isolated DNA was digested with MboI/HindIII and size fractionated on agarose gels. The DNA fragments were transferred to membranes and probed with the lambda specific sequences described above. The results of the DNA hybridization analysis are presented in FIG. 2.

In FIG. 2, the autoradiogram shown is of MboI/HindIII digested Hirt extracts, the 7.3 kb band represents DNA that has replicated one or zero times in human cells; the 2.2 kb band represents DNA that has replicated two or more times in human cells. M1 and M2 are size markers as in FIG. 1. The samples pHT17(+)/-pUHD15-1 and pHT17(−)/pUHD15-1 were co-transfected with 200 ng of pUHD15-1, a plasmid that expresses the tTA gene.

The tetracycline promoter had no effect on plasmid replication in the absence of the tTA protein (pHT17(+) and pHT17(−) (FIG. 2). However, when the plasmids were co-transfected with pUHD15-1 (Gossen, et al., 1992) replication activity was reduced by approximately 10-fold as compared to pHEN17 (FIG. 2, pHT17(+)/pHUD15-1 and pHT17(−)/pHUD15-1). The induced promoter inhibited replication in both orientations. Since replication was inhibited only when promoter activity was induced, these findings suggest that the inhibition of replication is due to promoter activity and not to a cis-acting effect of the promoter sequences.

EXAMPLE 6

REPLICATION ACTIVITY OF PLASMIDS CONTAINING THE TETRACYCLINE-RESPONSIVE PROMOTER

The effect of varying levels of tetracycline on the replication of a plasmid containing the tetracycline-responsive promoter was investigated as follows.

The plasmid pHT17(+) was co-transfected with pHUD15-1, the tTA expression vector, into 293S cells. Approximately 24 hours after transfection, cells were exposed to media containing various levels (0–10 µg/ml) of tetracycline. At 5 days post-transfection, samples were Hirt extracted and subjected to the MboI replication assay described above (Example 2). The results of the DNA hybridization analysis are presented in FIG. 3A.

In FIG. 3A, the autoradiogram shown is of MboI/HindIII digested Hirt extracts harvested five days post-transfection probes with the lambda specific sequences described above. In the figure, the 7.3 kb band represents DNA that has replicated one or zero times in human cells; the 2.2 kb band represents DNA that has replicated two or more times in human cells. M1 and M2 are size markers as in FIG. 1. The concentration of tetracycline, [Tc], is indicated for each sample. The tetracycline-responsive promoter was induced by co-transfection with 200 ng of pUHD15-1.

As a control for the possibility of direct effects of tetracycline on the replication activity of autonomous plasmids, a vector that contained no tetracycline-responsive promoter sequences, pHEN17, was co-transfected with the tTA expression vector, pUHD15-1. The assayed replication activity was then evaluated for varying levels of tetracycline.

Hirt extracts from transfected cells were harvested five days post-transfection and digested with MboI/HindIII. The digested DNA was size-fractionated on agarose gels and transferred to membranes. The membranes were probed as described above. The results of the hybridization analysis are presented in FIG. 3B. In the figure, the 7.3 kb band represents DNA that has replicated one or zero times in human cells; the 2.2 kb band represents DNA that has replicated two or more times in human cells. M1 and M2 are size markers as in FIG. 1. The concentration of tetracycline, [Tc], is indicated for each sample. The plasmid pHEN17 contains no tetracycline-responsive promoter sequences. As shown in FIG. 3B, tetracycline had no significant effect on the replication activity of the plasmid pHEN17.

Hybridization signals from the autoradiogram in FIG. 3A were quantitated by laser densitometry. These values were converted to Relative Replication Activity values, i.e., replicated DNA (2.2 kb band) divided by un-replicated DNA (7.3 kb). The Relative Replication Activity was plotted versus the tetracycline concentration. The graphed results are presented in FIG. 3C.

The data demonstrate that in the absence of tetracycline, there was a marked reduction in replication activity. The level of replication activity increased as the concentration of tetracycline in the media increased, and plasmid replication activity was completely restored at higher concentrations of tetracycline. Since tetracycline represses the activity of the tetracycline-responsive promoter, these results suggest that decreasing promoter activity is correlated with increasing replication activity.

EXAMPLE 7

ORIENTATION DEPENDENT REPLICATION AND TRANSCRIPTION TERMINATION

The effects of promoter elements on the replication of a plasmid that has been shown to replicate autonomously in both long- and short-term assays (Heinzel, et al., 1991) were evaluated.

The plasmids pBC17(+) and pBC17(-) (FIG. 4A) contain the CMV promoter element in both orientations located in the HindIII site of pBODY17 (Example 1). In FIG. 4A, the orientation of the CMV promoter is indicated for the two plasmids; the position of the upstream mouse sequence (UMS; Heard, et al., 1987; McGeady, et al., 1986; Salier, et al., 1989) in pBUC17(+) and pBUC17(-) is indicated; Hyg, hygromycin resistance gene and promoter; TK Term, thymidine kinase terminator; Family, family of repeats from EBV; H, HindIII; B, BamHI; S SalI.

These two plasmids, along with the positive control pBODY17 and the negative control pBODY, were transfected into 293S/EBNA (Heinzel, et al., 1991) cells. Replication was assayed directly at 5 days post-transfection using an MboI assay similar to the one described above (Example 2).

Hirt extracts from transfected cells were digested with MboI and EcoRI. The digestion products were size-fractionated on agarose gels. For each plasmid, digestion with EcoRI releases a common 2.3 kb band. Within this 2.3 kb band is a 0.8 kb MboI band. Thus, in an MboI/EcoRI digest, replicated DNA will produce a 0.8 kb band while un-replicated DNA will produce a 2.3 kb band. DNA was blotted to membranes from the agarose gels and probed with a radiolabeled 0.8 kb MboI fragment. The membranes were exposed to X-ray film. One resulting autoradiogram is shown in FIG. 4B.

In FIG. 4B, the 2.3 kb band represents DNA that has replicated one or zero times in human cells; the 0.8 kb band represents DNA that has replicated two or more times in human cells; M1 and M2 are size markers created by digesting pBODY with EcoRI (M1) and with EcoRI/DpnI (M2).

The results demonstrated that the positive control, pBODY17, showed a strong 0.8 kb band indicative of replication while the negative control, pBODY, showed little replication activity. The plasmids containing the CMV promoter element showed an inhibition of replication in an orientation-dependent manner. When the promoter was oriented in the positive direction (pBC17(+), FIG. 4B), replication activity was reduced by approximately 10-fold as compared to pBODY17. However, when the promoter was oriented in the negative direction (pBC17(-), FIG. 4B), little or no replication inhibition was observed.

When the CMV promoter was oriented in the negative direction, transcription proceeded in the same direction as transcription from the hygromycin resistance gene. A putative transcription termination sequence from the herpes simplex virus type I is located at the 3' end the hygromycin expression unit. The following experiments were performed to evaluate whether transcripts from the CMV promoter might be terminated at this sequence and whether this termination of transcripts in the negative direction might mitigate the inhibition of replication.

Plasmids were generated that had the upstream mouse sequence (UMS), which has been shown to efficiently terminate transcription in mammalian cells (Heard, et al., 1987; McGeady, et al., 1986; Salier, et al., 1989), cloned into the BamHI site adjacent to the CMV promoter (FIG. 4A). The plasmid pBUC17(+) has the UMS placed 350 bp downstream of the promoter, while in pBUC17(-), in which the CMV promoter is in the opposite orientation, the UMS is located 350 bp upstream of the promoter.

The data presented in FIG. 4B show that the replication activity of pBUC17(+) was 7-fold more than pBC17(+), which contains no transcription terminator sequences. Although replication activity was not fully restored (as compared to pBODY17), this result shows that a transcriptional terminator can mitigate the inhibition of replication by promoter elements, suggesting that transcription is directly involved in the inhibition of plasmid replication.

The replicating plasmids of the present invention are persistent in the nucleus over time. Plasmid DNA was detectable at 12 days post-transfection for all plasmids except pBC17(+), which was shown above to be replication deficient.

To confirm that transcription has a direct role in the inhibition of plasmid replication, the transcriptional activity and orientation of the CMV promoter/enhancer on these plasmids was qualitatively confirmed as follows. Total RNA was isolated from cells that had been transfected with selected plasmids. 20 μg of total RNA for each sample was slot-blotted onto a nylon membrane. Identical blots were probed with either a 2.2 kb fragment from the pBR region of the plasmid, or a 2.4 kb fragment from the promoter-proximal end of the human fragment 17. The results of this slot-blot analysis are presented in FIG. 4C.

In the figure, MOCK, corresponds to un-transfected cell sample; the location of the pBR and 17 probes used are indicated by brackets in FIG. 4A. The pBR probe shows a strong signal for pBC17(-), consistent with transcription directed by the CMV promoter in the negative direction. Since this plasmid was shown to replicate (FIG. 4B), this data suggests that transcription through this region does not inhibit replication, presumably due to the termination of transcription by the TK terminator.

The 17 probe shows a strong signal for pBC17(+), consistent with transcription from the CMV promoter oriented in the positive direction, while no signal is detected for the UMS-containing plasmid pBUC17(+) by the 17 probe. This result is consistent with the termination of transcripts emanating from the CMV promoter by the UMS. It is unlikely that the UMS is interfering with the activity of the CMV promoter, because it has been shown that the UMS has no negative effect on the activity of several other promoters (Salier, et al., 1989).

Taken together, the above data suggest that transcription from promoter elements is a factor in inhibiting plasmid replication.

EXAMPLE 8

MITIGATION OF REPLICATION INHIBITION BY THE UMS

The effect of the UMS on plasmids that contained no hygromycin transcription unit and no nuclear retention sequences was examined.

The plasmids pHUC17(+) and pHUC17(−) containing the UMS sequence located in the EcoRI site adjacent to the CMV promoter in pHC17(+) and pHC17(−) were generated (FIG. 1A). In the plasmid pHUC17(+) the UMS lies 30 bp upstream of the promoter, while in the plasmid pHUC17(−) the UMS lies 30 bp downstream of the promoter.

To control for any direct effects of the UMS on replication activity, the UMS was cloned into the negative control plasmid pHEN and the positive control plasmid pHEN17, to create pHENU and pHEN17U respectively. All of these plasmids were assayed for replication activity using the MboI assay described above (Example 2).

The results of a DNA hybridization analysis of MboI/HindIII digested Hirt extracts harvested five days post-transfection are presented in FIG. 5. In the figure, the 7.3 kb band represents DNA that has replicated one or zero times in human cells, the 2.2 kb band represents DNA that has replicated two or more times in human cells. M1 and M2 are size markers as in FIG. 1.

The control plasmids pHENU and pHEN17U indicate that the UMS has no direct effect on the replication activity of plasmids without promoter sequences. Consistent with the data shown in FIG. 1A, the data in FIG. 5 show that the plasmids carrying the CMV promoter/enhancer, pHC17(+) and pHC17(−), replicate poorly compared to pHEN17. When the UMS was situated upstream of the promoter in the plasmid pHUC17(+), replication was still inhibited. However, when the UMS was situated downstream of the promoter in pHUC17(−), replication activity increased by approximately 3-fold.

These results are consistent with those seen in FIG. 4B and suggest that the termination of transcripts can diminish the inhibition of replication by promoter sequences. Further, that the orientation effect observed in the pBODY17 plasmids was due to transcription termination by the TK terminator. The observation that the UMS does not increase replication activity when placed upstream of the promoter supports the idea that the UMS has no negative regulatory effect on the CMV promoter.

EXAMPLE 9

FURTHER VECTOR CONSTRUCTIONS

Figure 6:
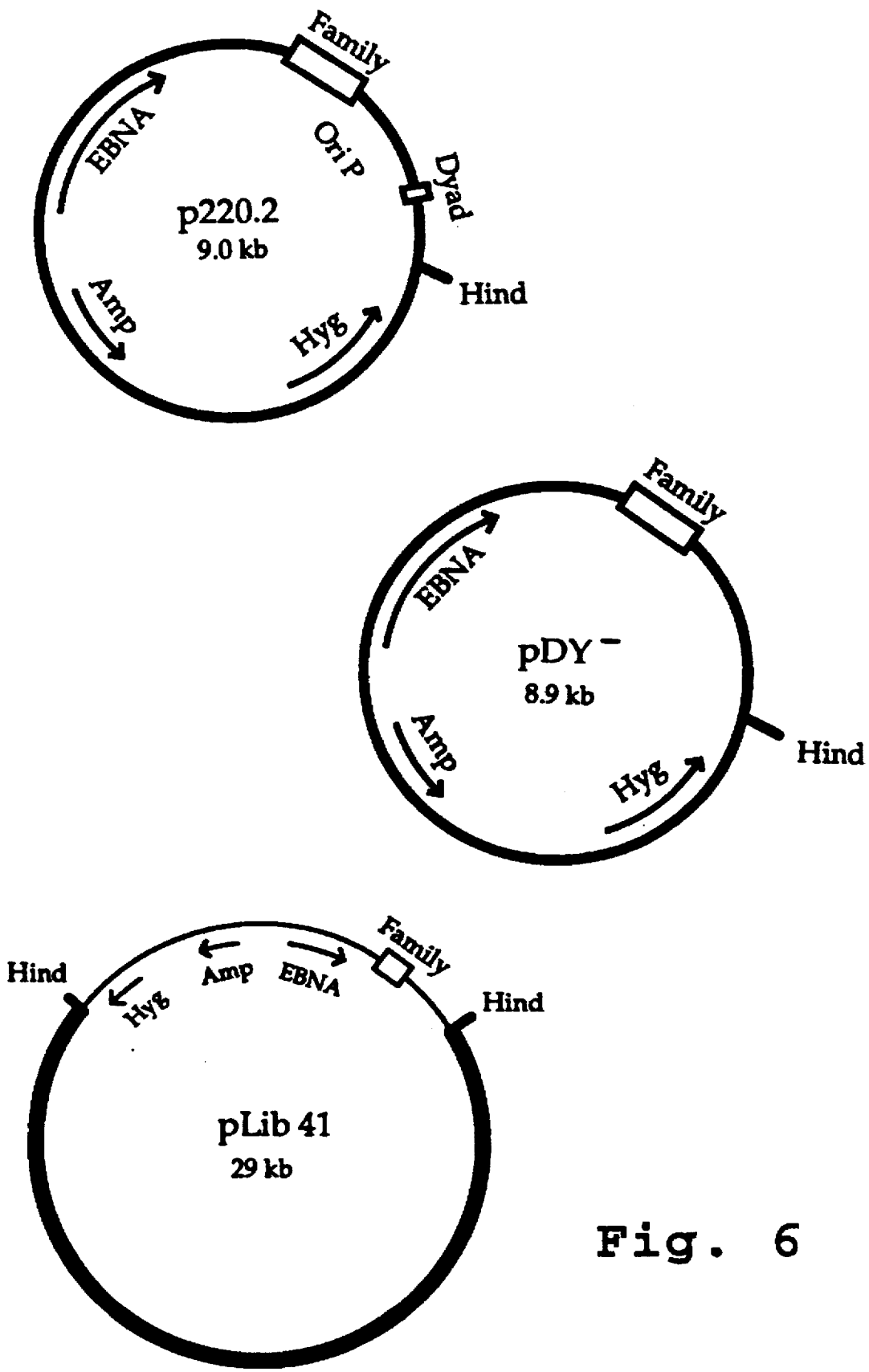
FIG. 6 presents plasmid maps for p220.2, pDY⁻ and pLIB41.

FIG. 6 illustrates the structure of the following three plasmids: p220.2, an Epstein Bar Virus (EBV) vector which is able to efficiently replicate as an extrachromosomal plasmid in human cells (Dubridge, et al., 1987); pDY⁻ constructed by removing the region of dyad symmetry from p220.2 (pDY⁻ is defective for replication in human cells) (Krysan, et al., 1989); pLIB41 is a pDY⁻ derivative which carries a 21-kb fragment of human DNA (Krysan, et al., 1989). pLIB41 replicates efficiently in human cells. The 21 kb human fragment is a randomly generated HindIII restriction fragment of human genomic DNA cloned into the HindIII site of pDY⁻ (Krysan, et al., 1989, herein incorporated by reference).

Further plasmids (described in Examples 10 to 13) that carry human DNA fragments have the same structure as pLIB41. All such plasmids carry human DNA cloned in the same position in the same vector as shown for pLIB41. In FIG. 6, the thick black line on the pLIB41 map represents the human DNA. EBNA=gene encoding EBNA-1. oriP=EBV origin of replication. Family=family of repeats from oriP. Dyad=region of dyad symmetry from oriP. Hyg$^R$=gene providing mammalian cells with resistance to the drug hygromycin. Ap$^R$=gene for ampicillin resistance in *E. coli*. H=recognition site for the restriction enzyme HindIII.

EXAMPLE 10

SHORT TERM REPLICATION ASSAYS FOR THE EXPRESSION OF VECTORS IN RODENT CELLS

Hamster BHK cells were transfected, as described above, with p220.2, pDY⁻, and pLIB41 the indicated plasmids. The transfected cells were grown for three days. DNA was isolated from the cells three days after transfection and digested with restriction endonucleases MboI/HindIII. MboI was used, as above, to distinguish replicated DNA from un-replicated. HindIII was used to linearize the 8.9-kb vector fragment common to the three plasmids.

Briefly, hamster BHK cells were grown in Dulbecco's-modified Eagle (Gibco-BRL) medium supplemented with 10% fetal calf serum, penicillin, and streptomycin. The cell cultures were grown at 37° C. in a 5% $CO_2$ incubator. Cells were split 1:20 into 60 mm tissue culture dishes containing fresh growth media one day prior to transfection, then transfected with 5 μg of each plasmid using Ca. phosphate co-precipitation (Wigler et al., 1979). One day after transfection, cells had reached confluency and were split 1:20 into 60 mm dishes containing fresh growth media.

After two days, low-$M_r$ DNA was extracted from the cells (Hirt, 1967). The Hirt extract from ⅓ of a 60 mm dish was treated with HindIII, MboI, and RNaseA and run on a 0.7% agarose gel. The DNA fragments were transferred to nylon membranes. The linearized 8.9-kb pDY⁻ vector was labeled by random primer extension (Pharmacia Biotechnology, Piscataway, N.J.) and used as the hybridization probe. The membrane was then washed and exposed to X-ray film as described (Krysan, et al., 1991). A photograph of the resulting autoradiogram is presented as FIG. 7.

In the figure, Marker 1=0.3 ng of pDY⁻ digested with HindIII; Marker 2=0.1 ng of pDY⁻ digested with DpnI. The arrow labeled NR (Not Replicated) points to the 8.9-kb HindIII fragment from pDY⁻ which results from plasmids which have replicated one or zero times in the hamster cells. The arrow labeled R (Replicated) points to the 2.8-kb MboI fragment of pDY− which is released from plasmids which have replicated two or more times in hamster cells.

Nearly all of the plasmid recovered from the cells transfected with pDY⁻ had replicated one or fewer times in the hamster cells. This result is similar to what was been seen when the pDY⁻ vector was transfected into human cells. This result is expected since pDY⁻ does not have a functional origin of replication.

FIG. 7 also reveals that p220.2 does not replicate any better than pDY⁻ does in hamster cells. Since p220.2 carries the complete EBV origin of replication, this result confirms that BHK cells are not permissive for EBV replication.

By contrast, roughly half of the plasmids recovered from the pLIB41 transfection have replicated two or more times in the hamster cells. This result indicates that our short-term assay can indeed detect replication and that the failure of p220.2 to replicate is not due to some limitation of the assay.

EXAMPLE 11

LONG-TERM REPLICATION IN HAMSTER CELLS

The following experiments demonstrated that the EBV nuclear retention function could act to stably maintain autonomously replicating, extrachromosomal plasmids in hamster cells.

The plasmids pDY⁻, p220.2, pLIB16, pLIB41, pDONUT-19A, and pDY-6α were transfected into hamster BHK cells. pLIB16 (14 kb human DNA insert), pDONUT-19A (19 kb human DNA insert) and pDY-6α (16 kb human DNA insert) are all derivatives of pDY⁻ which carry fragments of human DNA 14kb to 19kb long which have been shown to support autonomous replication in human cells (Krysan et al., 1989; 1993; Heinzel et al., 1991). The pDONUT vector is the same as pDY⁻, except that a NotI restriction endonuclease cut site has been added adjacent to the unique HindIII site of pDY⁻ (Heinzel, et al., 1991).

One day following transfection, cells were split the equivalent of 1:30 into 100 mm tissue culture dishes containing growth media plus 3 mg Hyg/ml. Cells were passaged in the presence of Hyg for 17 days, then low-M$_r$ DNA was Hirt extracted from the cells. Hirt extracts were subjected to DNA hybridization analysis as described in Example 10, with the exception that the samples were run on the gel either following treatment with MboI +RNaseA or RNaseA alone.

One portion of each DNA extract was run on an agarose gel without any restriction enzyme digestion. A second portion of each extract was treated with the enzyme MboI prior to electrophoresis. The DNA fragments were size fractionated on agarose gels, the fragments transferred to membranes, and then hybridized with a probe prepared from the pDY⁻ vector. The membrane was then exposed to X-ray film. A photograph of one such autoradiogram is presented in FIG. 8.

In the figure: Marker "−"=0.3 ng of uncut pLIB41. Marker "+"=0.1 ng of pLIB41 digested with DpnI. For each plasmid, the lane labeled "−" contains the undigested extract, and the lane labeled "+" contains the sample treated with MboI. The arrow labeled "Uncut circular plasmid" points to the super-coiled and nicked forms of the different plasmids. The arrow labeled "MboI digested" points to the 2.8-kb MboI fragment of the pDY⁻ vector which is released from plasmids which have replicated two or more times in hamster cells. The pDY⁻ plasmid was used as the hybridization probe for this experiment.

The marker lanes in FIG. 8 show pLIB41 running either as an uncut circular plasmid or after digestion with DpnI. The undigested sample demonstrates the position where super-coiled and nicked monomers of pLIB41 migrate on this gel. The DpnI-digested sample shows a 2.8 kb-fragment common to all of the plasmids used in this experiment. Since DpnI recognizes the same cleavage site as MboI, but cuts methylated DNA, this marker shows the position where plasmids which have replicated more than two times in the hamster cells will migrate on the gel following treatment with MboI.

There is no plasmid detectable in the extracts from the hamster cells transfected with p220.2 and pDY⁻. This finding supports that these plasmids replicate very poorly in the short-term replication assay described above. However, the four plasmids carrying large fragments of human DNA are present at an easily detectable level.

The undigested lanes for each sample show two distinct bands indicative of super-coiled and nicked circular plasmid. This result shows that the plasmids are maintained as extrachromosomal molecules. The MboI treated lanes show that all of the DNA detectable at this time has replicated two or more times in the hamster cells.

The above results indicate that the EBV nuclear retention function can operate in rodent cells and that large human DNA fragments provide efficient replication in rodent cells.

The copy number of each plasmid was determined by first calculating the total number of plasmids present in the MboI treated lane for each sample. Each MboI signal was compared to the signal for a known amount of DNA in the DpnI digested marker lane using a laser densitometer for autoradiogram exposure times in which the assay was approximately linear. Total plasmid number was divided by the number of cells used to generate each MboI signal, yielding the approximate copy number per cell. The copy numbers were in the range of 1 to 10 copies per cell.

EXAMPLE 12

DENSITY LABELING REPLICATION ASSAY

To determine if pLIB41 replicated in a controlled manner in hamster cells, a density shift assay was utilized to measure the number of times per cell cycle that pLIB41 replicated in BHK cells.

Hamster BHK [pLIB41]cells were split 1:15 into 60 mm dishes containing 2.5 ml fresh non-selective media/2.5 mls conditioned non-selective media/30 μg 5-bromo-2'-deoxyuridine (BrdU) per ml. At 12 and 24 h hours, DNA was Hirt extracted from the cells. The Hirt extract from ⅓ of a 60-mm dish was then treated with HindIII and RNaseA. The digested samples, in a volume of 125 μl, were added to a solution of $Cs_2SO_4$ which had a refractive index of 1.3715 (Szybalski, 1968). These samples were spun at 30,000 rpm in a Beckman VTi80 for approximately 48 h at 20° C.

Fractions were collected from the bottom of each gradient tube using a peristaltic pump. The fractions were then applied to a "ZETA PROBE" membrane (Bio-Rad, Richmond, Calif.) using a slot blot apparatus (made in Stanford Genetics shop). The membranes were hybridized with the following probes.

The results presented in FIG. 9A: the membrane was hybridized with $^{32}$P-labeled pDY⁻ plasmid and washed as described (Krysan, et al., 1991). The results presented in FIG. 9B: the membrane was then stripped and re-probed with a fragment of hamster genomic DNA which contains a copy of the hamster Alu repeat. In both figures: BHK=DNA extracted from BHK cells which do not carry any extrachromosomal plasmids. BHK [LIB41]=DNA extracted from BHK cells which carry the extrachromosomally replicating plasmid pLIB41. 0, 12, and 24 indicate the number of hours for which the given sample was grown in the presence of BrdU. LL=the gradient fractions which correspond to un-replicated, Light/Light DNA. HL=the gradient fractions which correspond to once or twice replicated Heavy/Light DNA. HH=the gradient fractions which correspond to twice replicated Heavy/Heavy DNA.

For the BHK cells which were not labeled with BrdU, all of the recovered plasmid banded in a single peak in the density gradient, corresponding to LL DNA (FIG. 9A). LL refers to the fact that neither of the DNA strands of the plasmid have incorporated the heavy thymidine analog BrdU.

For the cells grown in the presence of BrdU for 12 h, which corresponds to approximately one cell cycle, the majority of the recovered plasmid banded at an intermediate density, corresponding to HL DNA. These plasmids replicated once during the labeling period and therefore incorporated BrdU into one of their DNA strands. Some un-replicated plasmid was also detectable in the LL position for the 12-h labeling. None of the plasmid recovered from the twelve hour labeling was detectable at the HH position. Since the cell cycle time of BHK cells is approximately 12 h, this result indicates that pLIB41 is replicating in a controlled, once per cell cycle manner. The majority of the signal was present in the HL peak after a 12-h labelling, indicating that the plasmid was replicating with a high efficiency in the hamster cells.

For the cells grown in BrdU for 24 h, which corresponds to two complete cell cycles, the recovered plasmid was equally distributed between the HL and HH peaks of the density gradient. This result demonstrates that during this 24-h labeling, most of the plasmids replicate two times and are replicating with high efficiency.

The autoradiogram of the slot blot presented in FIG. 9A has a lane featuring DNA extracted from BHK cells which do not carry any pLIB41 plasmid. No signal was detectable in this lane. This control was included to demonstrate that the signal seen for the pLIB41 samples was not due to any cross-hybridization with the hamster genome.

The slot blot described above was stripped and re-probed with a hamster chromosomal sequence which contained a copy of the highly repetitive hamster Alu element (Caddle et al., 1990). This probing was done to monitor the extent to which the hamster chromosomes had replicated during the BrdU labeling periods.

Although the Hirt extraction protocol is designed to selectively isolate low molecular weight DNA, a significant amount of chromosomal DNA is also present in a Hirt extract. This chromosomal DNA is easily detectable by hybridization with a highly repetitive element such as the hamster Alu sequence.

The autoradiogram presented in FIG. 9B depicts the result of the Alu probing of the same slot blot seen in FIG. 9A. The BHK cells carrying no pLIB41 gave rise to a single peak at the LL position. This result demonstrates that chromosomal DNA can be detected in Hirt extracts. The patterns of replication seen using the chromosomal Alu probe at 0, 12, and 24-h labelings were similar to those seen with the plasmid probing. This result indicates that plasmid DNA is replicating in a manner similar to chromosomal sequences, suggesting high efficiency and once per cell cycle control.

No HH DNA was detectable for the twelve hour labeling. In addition, the twenty-four hour labeling showed approximately even amounts of HH and HL DNA. These results demonstrate that the cell cycle time of BHK cells is roughly 12 hours.

EXAMPLE 13

TRANSIENT DRUG RESISTANCE IN HAMSTER CELLS

The following experiments were performed to determine if (i) a biologically relevant level of EBNA-1 was being expressed in BHK cells transfected with p220.2, and (ii) EBNA-1 was required for the nuclear retention of autonomously replicating plasmids such as pLIB16.

The following plasmids were transfected into hamster BHK cells: pBODY, pDY$^-$, p220.2, pBODY-16, pLIB16. pBODY is a derivative of pDY$^-$ which does not carry the EBNA-1 gene. pBODY-16 is a derivative of pBODY which carries the 14-kb fragment of human DNA from pLIB16 which has been shown to support autonomous replication in human and hamster cells.

One day following transfection, the cells were split the equivalent of 1:30 into 100-mm tissue culture dishes containing growth media plus 3 mg Hyg/ml. The growth media was replaced every 2 days to ensure that a selective level of Hyg was maintained. Five days after plating into the Hyg-containing media, the media was removed from 1 plate from each transfection.

The cells on these dishes were then fixed and stained by adding a solution of 50% methanol/1% methylene blue to the dishes. The staining solution was removed from the dishes, and the dishes were rinsed with water to remove excess stain. The plates were then air-dried and photographed.

In addition, 5 days after transfection, further dishes of the cells which received pDY$^-$, p220, and pLIB16 were split 1:30 into fresh media containing Hyg. These cells were grown for another 5 days, at which point the cells were fixed, stained, and photographed as described above.

The stain allowed the visualization of any colony of BHK cells which had grown in the presence of Hyg. The pBODY and pBODY-16 transfections did not give rise to enough colonies at day 5 to allow the cells to be split for the day 10 analysis.

Only the cells transfected with pDY$^-$, p220.2, and pLIB16 resulted in a large number of drug resistant cells after the first five days of Hyg selection. This result suggests that the EBNA-1 gene is being expressed in hamster cells.

Cells transfected with pDY$^-$, p220.2, and pLIB16 were then grown for an additional five days under Hyg selection. The cells transfected with pLIB16 completely covered the plate at the ten day time point, consistent with the plasmid being efficiently replicated and maintained as an extrachromosomal molecule. By contrast, cells transfected with p220.2 and pDY$^-$ were sparse at day ten. This result is consistent with defective replication of these plasmids in hamster cells.

These results demonstrate that p220.2 and pDY$^-$ give rise to the characteristic transient drug resistance phenotype in hamster cells, indicating that EBNA-1 is being expressed. The observation that p220.2 behaves the same as pDY$^-$ further supports the conclusion that hamster cells are not permissive for EBV replication.

EXAMPLE 14

CHLORAMPHENICOL ACETYLTRANSFERASE GENE EXPRESSION IN VIVO

A. TISSUE SPECIFIC EXPRESSION OF CAT

The in vivo expression of the chloramphenicol acetyltransferase gene, carried in a vector of the present invention, is evaluated essentially as described by Zhu, et al. (1993).

A vector is constructed, following the guidance of the present invention, capable of replication in rodent cells and containing the chloramphenicol acetyltransferase gene in an expression cassette. For example, an expression cassette is constructed containing the CMV promoter adjacent CAT coding sequences, similar to the CMV/CAT cassette used in Zhu, et al. (1993). The CMV/CAT construct may be flanked by UMS elements. This expression cassette is then cloned in the NruI site of pLIB41. This construct is designated pLIB41-CAT.

The plasmid is mixed with liposomes that have a net cationic charge, for example, containing N[1-(2,3-dioleyloxy)propyl]-N,N,N-trimethylammonium chloride (DOTMA) (Felgner, et al., 1987) and dioleoyl phosphatidylethanolamine (DOPE) in a 1:1 ratio. Liposomes can be made by any of numerous methods known to one skilled in the art (e.g., Debs, et al., 1990; U.S. Pat. No. 4,897,355, Eppstein, D., et al., issued 30 Jan. 1990; and U.S. Pat. No. 4,394,448, Szoka, F., et al., issued 19 Jul. 1983).

The ratio of DNA to liposomes is typically 1 μg:8 nmol. Briefly, 100 μg of plasmid pLIB41-CAT complexed with 800 nmoles of liposome composition is injected into the tail veins of female ICR mice (Simonson Labs, Gilroy, Calif.). The pLIB41-CAT/DOTMA:DOPE liposome mixture is typically injected in 200 μl of 5% dextrose in water. Mice are sacrificed after 48 hours and various tissues harvested and homogenized. Tissue extracts are prepared by standard procedures and total protein of the extracts is determined by using a protein assay (e.g., Bio-Rad, Richmond, Calif.; Coomasie assay). Each tissue extract is normalized for total protein concentration and assayed for CAT activity as previously described (Gorman, et al., 1982). Zhu, et al., employed the following modification for CAT assays: 0.3 μCi of $^{14}$C-labeled chloramphenicol (55 mCi/mmol) was added to 200 nmol of acetyl coenzyme A for a final volume of 122 μl. The results demonstrate the tissue specific levels of CAT gene expression.

The relative concentrations of DNA and liposomes can be varied in the above procedure to determine optimal proportions for delivery to selected tissues. For example, ICR mice are given a tail-vein injection of 50, 100, or 150 mg of plasmid DNA complexed to 400, 800, or 1200 nmol of DOTMA:DOPE liposomes, respectively.

For the quantitation of CAT activity in tissue extracts, areas corresponding to [$^{14}$C]chloramphenicol and its acetylated derivatives are scraped from the thin-layer chromatography plates and subjected to scintillation counting. Enzymatic activity of CAT in the extracts is typically expressed as picomoles of [$^{14}$C]chloramphenicol acetylated per milligram of protein per hour under assay conditions.

Control mice are injected with un-modified pLIB41 complexed with the same liposomes at the same concentrations.

The above assays to determine tissue specific expression of the CAT from the pLIB41-CAT vector are usually performed in triplicate for any given DNA/liposome ratio and any selected tissue.

DNA HYBRIDIZATION AND DNA AMPLIFICATION ANALYSES OF MOUSE TISSUES FOR THE DETECTION OF THE CAT GENE

Mice are injected with the DNA/liposome complexes as described above. At 1 and 20 days tissues are removed and nuclear DNA isolated (Feinstein, et al., 1982). For DNA hybridization analysis, the DNA from each tissue sample is digested with (i) a restriction endonuclease that does not cut within the plasmid, and MboI/HindIII (Example 2). The resulting DNA fragments are size fractionated by electrophoresis on a 1% agarose gel. The DNA fragments are transferred to membranes and probed as described above using a labeled vector specific probe. The blot is washed and rehybridized with a $^{32}$P-labeled BamH1-Pst1 fragment of the mouse β-globin gene to detect mouse genomic DNA.

The above-described DNA analysis provides information concerning the continued presence of the plasmid in tissue over time. Further, the MboI/HindIII digestion and hybridization results demonstrate whether the plasmid has replicated in each tissue cell type.

Polymerase chain amplification reactions are also used to detect the presence of the CAT gene in tissue samples. DNA is extracted from various tissues (e.g., lung, lymph nodes, heart, and spleen) of animals injected with the DNA/liposome complex and of control animals. The DNA samples are then used in polymerase chain amplification reactions (Mullis; Mullis, et al.) using, for example, the following CAT specific primers (Zhu, et al., 1993): SEQ ID NO:1, ACGTTTCAGTTTGCTCAGGG and SEQ ID NO:2, AGCTAAGGAAGCTAAAATGG. Amplification using these primers results in a 320 base pair fragment product when the pLIB41-CAT plasmid is present in the tissue sample DNA.

Amplification reagents are obtained from Perkin Elmer/Cetus (Norwalk, Conn.), and reactions are carried out per the manufacturer's instructions.

C. LONG TERM VECTOR EFFECTS.

Mice are also sacrificed at longer time points after injection of the plasmid/liposome mixtures. Mice are sacrificed at weekly intervals for eight weeks or longer, to demonstrate the longevity of CAT activity generated by the autonomously replicating plasmids of the present invention.

Genes of interest in gene therapy, such as the cystic fibrosis transmembrane conductance regulator gene (Riordan et al., 1989) can be used to replace the CAT gene in the autonomously replicating vector and delivered to animals or humans using liposome delivery by injection (Zhu et al., 1993), aerosol (Stribling et al., 1992), or other delivery means.

The long-term replication and retention of the vectors of the present invention gives rise to long-term delivery of the desired gene product to tissues of interest. This result is superior to that of vectors that cannot replicate well or be retained by mammalian cells for long periods of time.

General techniques for the manipulation of mouse embryos, for the generation of transgenic animals, are known in the art (e.g., Hogan, et al., 1986)

While the invention has been described with reference to specific methods and embodiments, it will be appreciated that various modifications and changes may be made without departing from the invention.

It is claimed:

1. An expression useful for transfection of a host cell, comprising
   an Epstein Barr Virus (EBV) family of repeats,
   a copy of the EBV Nuclear Antigen-1 (EBNA-1) gene that can be functionally expressed in the host cell,
   a eucaryotic DNA fragment, which provides the ability of the vector to replicate in host cells, and
   an expression cassette which comprises a promoter functional in said host cell, a coding sequence having 5' and 3' ends, where said coding sequence is functionally linked to said promoter, where said 5' end is adjacent the promoter and said 3' end is adjacent transcription termination sequences.

2. The vector of claim 1, where said eucaryotic DNA fragment is randomly generated from human genomic DNA.

3. The vector of claim 1, which further includes DNA sequences that allow the propagation of the vector in a secondary host.

4. The vector of claim 1, where said vector further includes an expression cassette where said coding sequence encodes a gene useful for genetic selection in the host cell.

5. The vector of claim 1, where the coding sequence in said expression cassette is a reporter gene.

6. The vector of claim 1, where, in said expression cassette, said promoter is a cytomegalovirus promoter and said transcription termination sequences are upstream mouse sequences (UMS) or SV40 transcription termination sequences.

7. The vector of claim 1, wherein said coding sequence in said expression cassette encodes a polypeptide.

8. The vector of claim 1, wherein said coding sequence in said expression cassette encodes an RNA product.

9. A host cell transfected with the vector of claim 1.

10. The vector of claim 2, where said fragment is between about 8 and 20 kilobases.

11. The vector of claim 3, where said DNA sequences include an origin of replication and a selectable marker.

12. The vector of claim 11, where said secondary host is bacterial.

13. The vector of claim 4, where expression of the gene confers hygromycin resistance.

14. The vector of claim 5, where said reporter gene encodes chloramphenicol acetyl transferase, β-galactosidase, or luciferase.

15. The vector of claim 8, wherein said coding sequence in said expression cassette encodes an antisense RNA.

16. The vector of claim 8, wherein said coding sequence in said expression cassette encodes a ribozyme.

17. The host cell of claim 9, where said host is a mammalian cell.

18. A method for expression of a protein in a host cell, comprising
   transfecting said host cell with the vector of claim 7, and
   culturing the host cell under suitable conditions so that the polypeptide is produced by said cell.

19. A method of claim 18, where said host cell is a mammalian cell.

20. A method of claim 18, which further includes isolating the polypeptide from the cell.

21. A method of producing a stably transformed mammalian cell, comprising
   (i) selecting a mammalian host cell,
   (ii) preparing an expression vector which comprises
      an Epstein Barr Virus (EBV) family of repeats,
      a copy of the EBV Nuclear Antigen-1 (EBNA-1) gene that can be functionally expressed in the host cell, a eucaryotic DNA fragment, which provides the ability of the vector to replicate in host cells, and an expression cassette which comprises a promoter functional in said host cell, a coding sequence having 5' and 3' ends, where said coding sequence is functionally linked to said promoter, where said 5' end is adjacent to the promoter and said 3' end is adjacent to transcription termination sequences, (iii) introducing said expression vector into the host cell, and (iv) maintaining the host cell into which said expression vector has been introduced.

22. The method of claim 21, where said mammalian cell is a rodent cell.

23. The method of claim 21, where said cell is a human cell.

24. The method of claim 21, where said maintaining includes culturing the cell in vitro.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer 1

( x i ) SEQUENCE DESCRIPTION: SEQ ID NO:1:

ACGTTTCAGT TGCTCAGGG      20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA ( i i i ) HYPOTHETICAL: NO ( i v ) ANTI-SENSE: NO ( v i ) ORIGINAL SOURCE:
    ( C ) INDIVIDUAL ISOLATE: Primer 2

( x i ) SEQUENCE DESCRIPTION: SEQ ID NO:2:

AGCTAAGGAA GCTAAAATGG      20